US009224962B2

(12) United States Patent
Yam et al.

(10) Patent No.: US 9,224,962 B2
(45) Date of Patent: Dec. 29, 2015

(54) DENDRIMERS CONTAINING LUMINESCENT GOLD (III) COMPOUNDS FOR ORGANIC LIGHT-EMITTING DEVICES AND THEIR PREPARATION

(71) Applicants: Vivian Wing Wah Yam, Hong Kong (CN); Kobe Man Chung Tang, Hong Kong (CN); Maggie Mei Yee Chan, Hong Kong (CN); Keith Man Chung Wong, Hong Kong (CN)

(72) Inventors: Vivian Wing Wah Yam, Hong Kong (CN); Kobe Man Chung Tang, Hong Kong (CN); Maggie Mei Yee Chan, Hong Kong (CN); Keith Man Chung Wong, Hong Kong (CN)

(73) Assignee: The University of Hong Kong, Hong Kong (HK)

( * ) Notice: Subject to any disclaimer, the term of this patent is extended or adjusted under 35 U.S.C. 154(b) by 296 days.

(21) Appl. No.: 13/779,021

(22) Filed: Feb. 27, 2013

(65) Prior Publication Data
US 2013/0228758 A1 Sep. 5, 2013

Related U.S. Application Data

(60) Provisional application No. 61/605,553, filed on Mar. 1, 2012.

(51) Int. Cl.
| | | |
|---|---|---|
| H01L 51/00 | (2006.01) |
| G05D 21/00 | (2006.01) |
| G06Q 10/10 | (2012.01) |
| G06Q 50/02 | (2012.01) |

(52) U.S. Cl.
CPC ............ H01L 51/0084 (2013.01); G05D 21/00 (2013.01); G06Q 10/10 (2013.01); G06Q 50/02 (2013.01)

(58) Field of Classification Search
CPC .................................................. H01L 51/0084
USPC .............................................. 257/40; 546/4
See application file for complete search history.

(56) References Cited

U.S. PATENT DOCUMENTS

2010/0148663 A1* 6/2010 Tsai et al. ..................... 313/504

OTHER PUBLICATIONS

Au et al., "Luminescent Cyclometalated Dialkynylgold(III) Complexes of 2-Phenylpyridine-Type Derivatives with Readily Tunable Emission Properties," Chem. Eur. J., 2011, 17, 130-142.*

Primary Examiner — Ling-Siu Choi
Assistant Examiner — Catherine S Branch
(74) Attorney, Agent, or Firm — Kelly & Krause, L.P.; W. Dennis Drehkoff

(57) ABSTRACT

A novel class of saturated or conjugated dendrimers containing at least one strong σ-donating group coordinated to cyclometalated tridentate gold(III) compounds having the chemical structure depicted by generic formula:

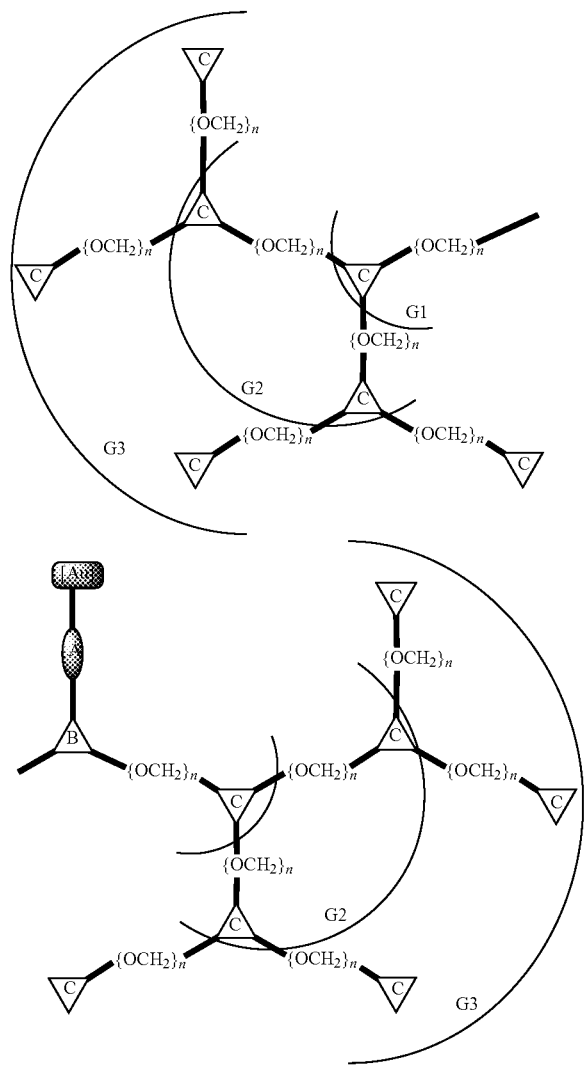
wherein:
 (a) [Au] is a cyclometalated tridentate gold(III) group;
 (b) Unit A is a σ-donating chemical group;
 (c) Unit B is a central part of the dendrons comprising a branch point of component dendrimers;
 (d) Unit C is optional surface groups or dendrons of the dendrimers;
 (e) n=0 or 1.
20 Claims, 15 Drawing Sheets

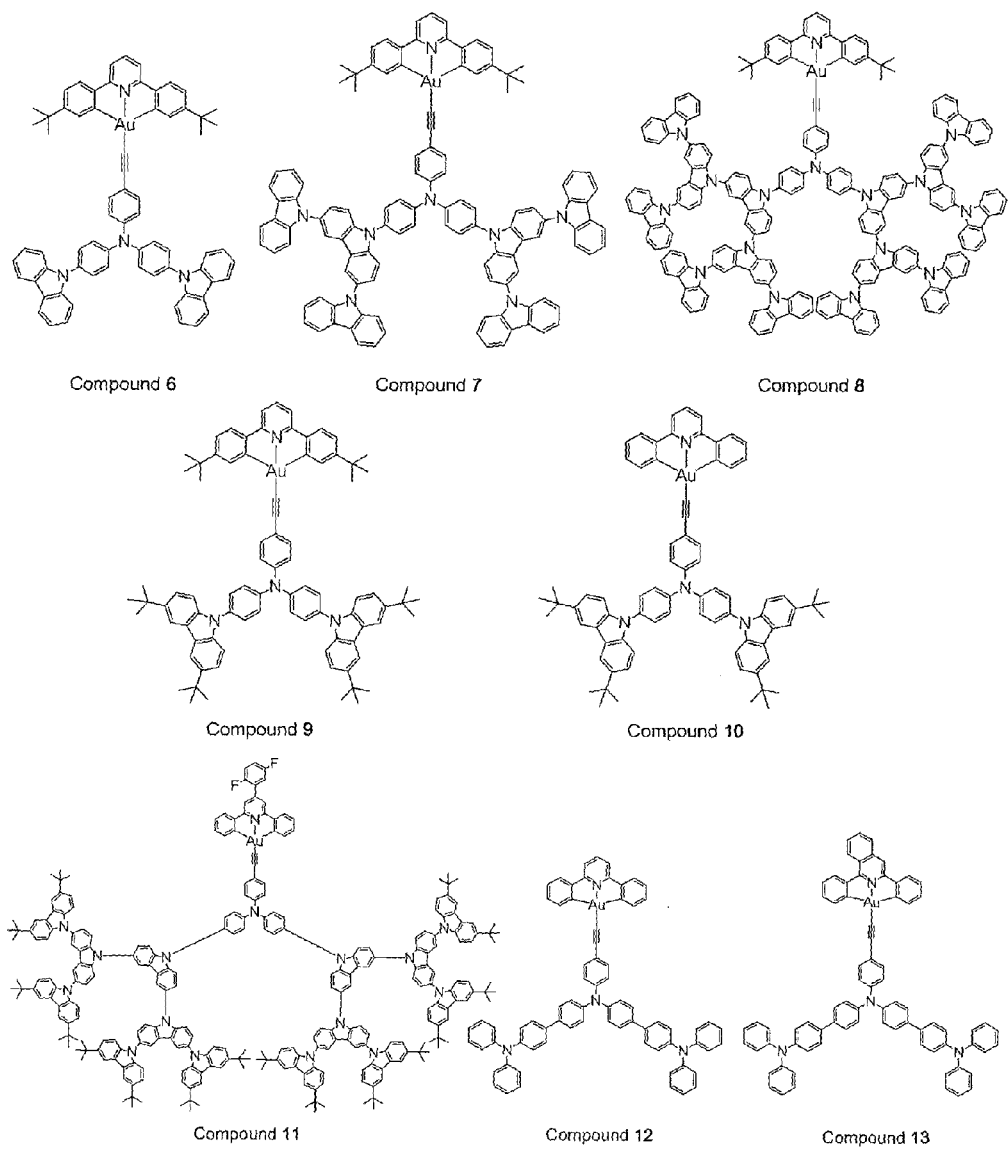
Scheme 1
FIG. 1.1

DENDRIMERS CONTAINING LUMINESCENT GOLD (III) COMPOUNDS FOR ORGANIC LIGHT-EMITTING DEVICES AND THEIR PREPARATION

This non-provisional application is based on and claims priority to the U.S. Provisional Application Ser. No. 61/605,533 filed on Mar. 1, 2012.

FIELD OF THE INVENTION

Embodiments of the invention are directed to a novel class of dendrimers containing cyclometalated tridentate gold(III) compounds and the syntheses of these compounds. These solution-processable compounds can be used as light-emitting material in phosphorescent organic light-emitting devices (OLEDs).

BACKGROUND OF THE INVENTION

With the advantages of low cost, light weight, low operating voltage, high brightness, robustness, color tunability, wide viewing angle, ease of fabrication onto flexible substrates as well as low energy consumption, OLEDs are considered to be remarkably attractive candidates for flat panel display technologies and for solid-state lighting. Phosphorescent heavy metal complexes are an important class of materials in making OLEDs because of their relatively long triplet excited-state luminescence lifetimes and high luminescence quantum yields. The presence of a heavy metal center can effectively lead to a strong spin-orbit coupling and thus promotes an efficient intersystem crossing from its singlet excited state, eventually to the lowest-energy triplet excited state followed by relaxation to the ground state via phosphorescence at room temperature. This results in a four-fold enhancement on the internal quantum efficiency of the OLEDs up to 100%.

Typically an OLED consists of several layers of semiconductor sandwiched between two electrodes. The cathode is composed of a low work function metal or metal alloy deposited by vacuum evaporation, whereas the anode is a transparent conductor such as indium-tin oxide (ITO). Upon the application of a DC voltage, holes injected by the ITO anode and electrons injected by the metal cathode will recombine to form excitons. Subsequent relaxation of excitons will then result in the generation of electroluminescence.

The breakthroughs that led to the exponential growth of this field and to its first commercialized products can be traced to two pioneering demonstrations. In 1987, Tang and VanSlyke [Tang, C. W.; VanSlyke, S. A. *Appl. Phys. Lett.* 51, 913 (1987)] proposed the use of a double-layer structure of vacuum deposited, small-molecular films, in which tris(8-hydroxyquinoline)aluminum($Alq_3$) was utilized both as light emitting layer and electron transporting layer. Later, the first polymeric light emitting device was pioneered by Burroughs et al. in 1990 [Burroughs, J. H.; Bradley, D. D. C.; Brown, A. R.; Marks, N.; Friend, R. H.; Burn, P. L.; Holmes, A. B. *Nature* 347, 539 (1990)], in which a yellow-green electroluminescence from poly(p-phenylenenvinylene) (PPV) was achieved. Since then, a number of new electroluminescent small molecular based and polymeric light emitting materials have been investigated with improved light emitting properties. The key advantage of using polymers as light emitting materials is that they are highly soluble in most organic solvents, and the devices can be easily fabricated by using low-cost and efficient wet processing techniques, such as spin-coating, screen-printing, or ink-jet printing [Burrows, P. E.; Forrest, S. R.; Thompson, M. E. *Curr. Opin. Solid State Mat. Sci.* 2, 236 (1997)].

Apart from the development of small molecular and polymeric materials, recent demonstrations of the design and synthesis of dendrimers as light emitting materials provide new and interesting observations. Dendrimers are branched macromolecules consisting of repetitive units (dendrons) having a well-defined size and number of peripheral groups. These materials are typically comprised of three parts: a core unit, surrounding dendrons, and peripheral groups. The branching levels of the surrounding dendrons determine the dendrimer generation, in which the peripheral groups attached onto the surface of the surrounding dendrons can control the intermolecular interactions, solubility, viscosity and processability of the dendrimers. The emissive chromophores of the dendrimers can be located at the core of the dendrimer, within the surrounding dendrons or at the peripheral groups of the dendrimers. Typically, emissive chromophores are attached at the core units. In general, dendrimers can be divided into two classes, conjugated dendrons and saturated dendrons. The branching point of the conjugated dendrons or dendrimers must be fully conjugated but not essentially delocalized [Burn, P. L.; Lo, S. C.; Samuel, I. D. W. *Adv. Mater* 19, 1675 (2007)].

The distinct properties of dendrimers allow them to be good candidates in making OLEDs. Unlike polymers, dendrimers show a well-defined structure and precise molecular weight, in which the purity of the products can be well controlled and are reproducible; both of which are crucial factors for commercialization. In addition, their high solubility in most organic solvents opens up a possibility to fabricate the devices by solution-processed techniques such as spin-coating and ink jet printing. Such techniques not only are essential for the patterning of large-area displays and solid-state lighting panels, but also avoid the use of the expensive high-temperature vacuum evaporation techniques that are needed for preparing small molecular based OLEDs. More importantly, the dendrimer generation can control the intermolecular interactions. Intermolecular interactions are well-known to have an influence on the efficiency of OLEDs. Indeed, many emitters show strong luminescent properties in solution. However, the strong intermolecular interactions present in the solid state lead to the formation of dimers, excimers or aggregates that lower the efficiency of the OLEDs. At high current density, triplet-triplet annihilation tends to further lower device performance. In view of these properties, the introduction of bulky peripheral groups can keep the molecules apart and thereby avoid these problems. Furthermore, the color of light emission can be fine-tuned by simply choosing different combinations of the cores, dendrimers, and type of peripheral groups. For instance, compounds with the same branching level of surrounding dendrons and surface groups attached to different cores can lead to different color emission. The glass transition temperature of these macromolecules is usually high, giving a good operation stability to the devices [Liu, D.; Li, J. Y. J. *Mater. Chem.* 19, 7584 (2009)].

The first OLED with dendrimers as light emitting materials was demonstrated by Wang et al. [Wang, P. W.; Liu, Y. J.; Devadoss, C.; Bharathi, P.; Moore, J. S. *Adv. Mater* 8, 237 (1996)]. These dendrimers contained a highly fluorescent core, 9,10-bis(phenylethynyl)-anthracene, phenylacetylene as surrounding dendrons for electron capture, and tertiary butyl groups as the peripheral groups that maintained its solubility. Such devices exhibited two major photoluminescence bands at 480 and 510 nm, and a broad, structureless emission band at 600 nm; however, the device performance was rather low and indeed no efficiency data was reported.

Later, Halim et al. reported a family of conjugated light emitting dendrimers based on PPV structure [Halim, M.; Pillow, N. G; Samuel, I. D. W.; Burn, P. L. *Adv. Mater* 11, 371 (1999)]. These dendrimers consisted of a distyrylbenzene core for blue color emission, stilbene dendrons, and t-butyl peripheral groups for solution processing properties. All three generations of dendrimers could be spin-coated from a chloroform solution to form amorphous thin films that produced a blue emission in the photoluminescence spectrum. A red shift was observed in the electroluminescence spectrum for the first generation dendrimer. With increasingly bulky groups to form different generations of dendrimers, concentration quenching effects were substantially suppressed. This demonstrated that dendrimers can effectively prevent the intermolecular interactions and the formation of dimers, excimers or aggregates.

While solution-processable fluorescent OLEDs have been realized, their efficiencies are usually quite low, and can be as low as 0.1%. In order to improve the device performance, it is desirable to make use of spin-orbit coupling in order to mix both singlet and triplet excited states. Hence, the use of heavy metal complexes in OLEDs is preferred over purely organic materials. Recently, a series of green-emitting carbazole conjugated dendrimers containing iridium(III) complexes have been reported by Ding et al. [Ding, J. Q.; Gao, J.; Cheng, Y.; Xie, Z; Wang, L. X.; Ma, D.; Jing, X. B.; Wang, F. S. *Adv. Funct. Mater.* 16, 571 (2006)]. By taking advantage of the dendritic structure(s), high solubility, non-doped, low cost solution-processable OLEDs had been achieved. By increasing the size of the dendrons, the intermolecular interactions can be significantly reduced, and good hole-transporting properties of carbazoles can be obtained. Superior device performance including peak external quantum efficiency (EQE) of 10.3% and current efficiency (CE) of 34.7 cd $A^{-1}$ were achieved for a non-doped green OLED. Red-emitting triphenylamine dendrimers containing iridium(III) complexes were also reported in 2007 [Zhou, G. J.; Wang, W. Y.; Yao, B.; Xie, Z. Y.; Wang, L. X. *Angew. Chem. Int. Ed.* 46, 1149 (2007).] The extended π-conjugated system of triphenylamine dendrons raises the highest occupied molecular orbital (HOMO) level, and the electron-rich triphenylamine moieties facilitate an efficient hole injection from the anode. High EQE and CE of the devices of 7.4% and 3.7 cd $A^{-1}$, respectively, were reached, even higher or comparable to the vacuum deposited devices with similar Commission Internationale de L'Eclariage (CIE) color. This indicates that dendrimers are one class of the promising light emitting materials for solution-processable OLEDs.

Even though there has been an increased interest in electrophosphorescent materials, particularly metal complexes with heavy metal centers, most of the development work has been focused on the use of iridium(III), platinum(II) and ruthenium(II), whereas the use of other metal centers has been much less explored. In contrast to the isoelectronic platinum(II) compounds which are known to exhibit rich luminescence properties, very few examples of luminescent gold(III) complexes have been reported, probably due to the presence of low-energy d-d ligand field (LF) states and the electrophilicity of the gold(III) metal center. One way to enhance the luminescence of gold(III) complexes is through the introduction of strong σ-donating ligands, which was first demonstrated by Yam et al. in which stable gold(III) aryl compounds were synthesized and found to display interesting photoluminescence properties even at room temperature [Yam, V. W. W.; Choi, S. W. K.; Lai, T. F.; Lee, W. K. *J. Chem. Soc., Dalton Trans.* 1001 (1993)]. Afterward, Yam et al. synthesized a series of bis-cyclometalated alkynylgold(III) compounds using various strong σ-donating alkynyl ligands, and all these compounds were found to exhibit rich luminescence behaviors at both room and low temperatures in various media [Yam, V. W.-W.; Wong, K. M.-C.; Hung, L.-L.; Zhu, N. *Angew. Chem. Int. Ed.* 44, 3107 (2005); Wong, K. M.-C.; Hung, L.-L.; Lam, W. H.; Zhu, N.; Yam, V. W.-W. *J. Am. Chem. Soc.* 129, 4350 (2007); Wong, K. M.-C.; Zhu, X.; Hung, L.-L.; Zhu, N.; Yam, V. W.-W.; Kwok, H. S. *Chem. Commun.* 2906 (2005)]. Very recently, a new class of phosphorescent material of cyclometalated alkynylgold(III) complexes has been reported and fabricated by vapor deposition [Au, V. K.-M.; Wong, K. M.-C.; Tsang, D. P.-K.; Chan, M. Y.; Yam, V. W.-W. *J. Am. Chem. Soc.* 132, 14273 (2010)]. The optimized OLED reached a EQE of 11.5% and CE of 37.4 cd $A^{-1}$. This suggested that the alkynylgold(III) complexes are promising phosphorescent materials in terms of efficiency and thermal stability.

The present invention discloses herein the design, synthesis and photoluminescence behaviour of luminescent gold (III) dendrimers, and their device fabrication using solution-processing techniques to produce high efficiency dendrimer OLEDs. These devices combine saturated and conjugated dendrimers, containing at least one strong σ-donating group and a cyclometalated tridentate gold (III) compound. These novel devices can be fabricated using low cost, high efficiency, solution-processing techniques to obtain phosphorescence-based OLEDs that do not exhibit the limitations of known OLEDs.

BRIEF SUMMARY OF THE INVENTION

Embodiments of the invention are directed to novel luminescent cyclometalated gold(III) dendrimers and their preparation. Other embodiments of the invention are directed to OLEDs from the novel luminescent gold(III) dendrimers.

The novel luminescent gold(III) dendrimers are either saturated or conjugated dendrimers containing one strong σ-donating group coordinated to a gold(III) metal center.

The novel luminescent gold(III) dendrimers have the chemical structure shown in the generic formula,

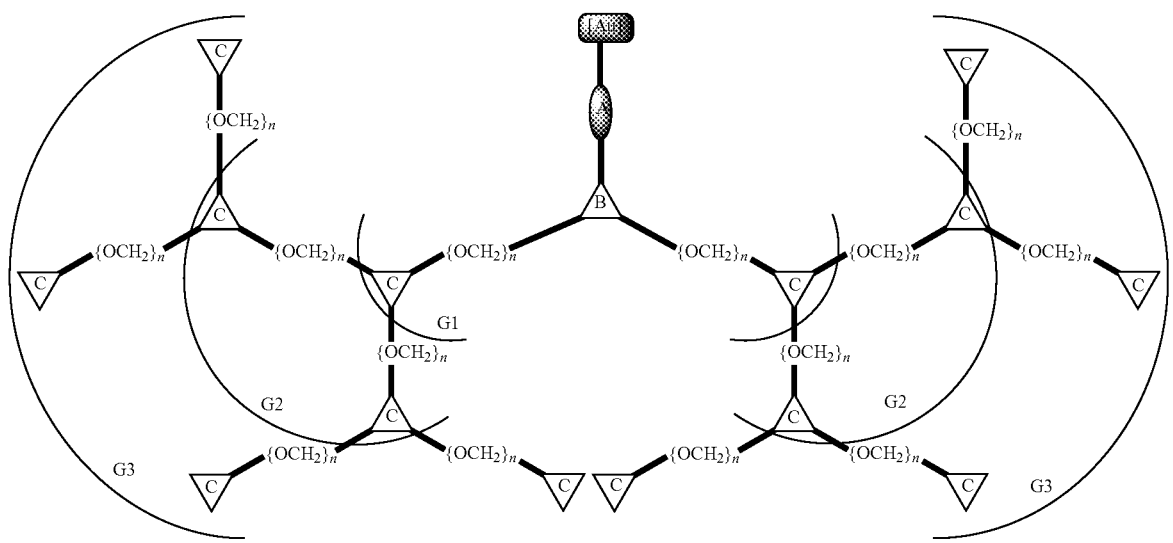

wherein:
(a) [Au] is a cyclometalated tridentate gold(III) group;
(b) Unit A is a σ-donating chemical group;
(c) Unit B is a central part of the dendrons comprising a branch point of component dendrimers;
(d) Unit C is optional surface groups or dendrons of the dendrimers;
(e) n=0 or 1.

In accordance with the present invention, these novel luminescent gold(III) dendrimers, show either strong photoluminescence via a triplet excited state upon photo-excitation, or electroluminescence via a triplet exciton upon applying a DC voltage. These compounds according to embodiments of the invention are highly soluble in common organic solvents such as dichloromethane and chloroform. Alternatively, the compounds can be doped into a host matrix for thin film deposition by spin-coating or ink-jet printing or other known fabrication methods. In some embodiments of the compounds can be used for the fabrication of OLEDs as phosphorescent emitters or dopants to generate electroluminescence.

As shown in FIG. 2, according to one embodiment of the present invention, the cyclometalated gold(III) dendrimers are included in light-emitting layer 106 of OLED 100. OLED 100 further comprises a layered structure having cathode layer 102, electron transporting layer 104, luminescent gold (III) compound as light-emitting layer 106, hole-transporting layer 108, and anode 110 deposited on glass substrate 112.

BRIEF DESCRIPTION OF THE DRAWINGS

FIG. 1.1 shows the chemical structures of compounds 6-13 in Scheme 1.

Figure 1:
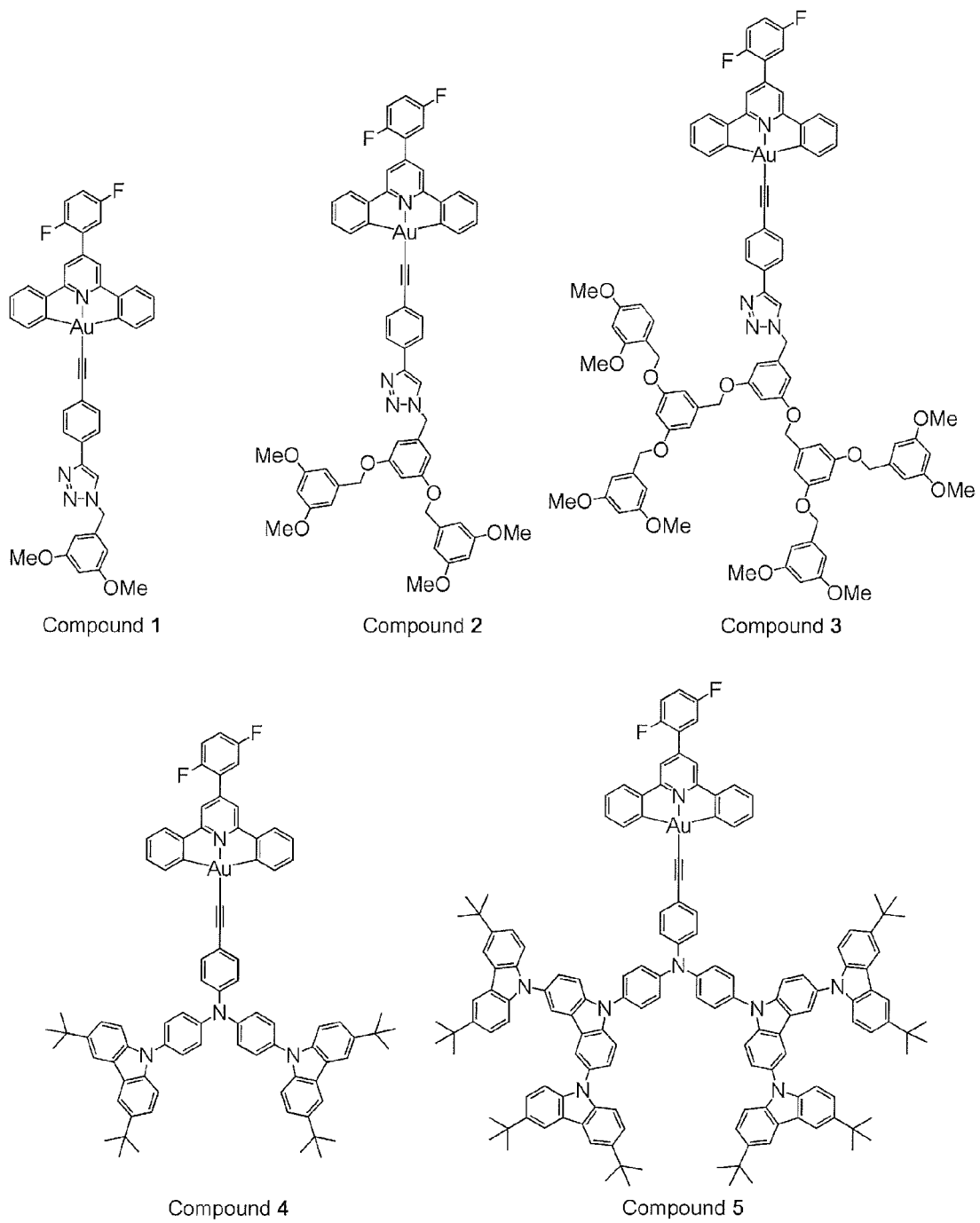
FIG. 1 shows the chemical structures of compounds 1-5 in Scheme 1.

DETAILED DESCRIPTION OF THE INVENTION (1) The present invention is directed to the synthesis and luminescence studies of novel classes of saturated and conjugated dendrimers containing one strong σ-donating group coordinated to the cyclometalated tridentate gold (III) metal centre. The compounds have the chemical structure shown in generic formula,

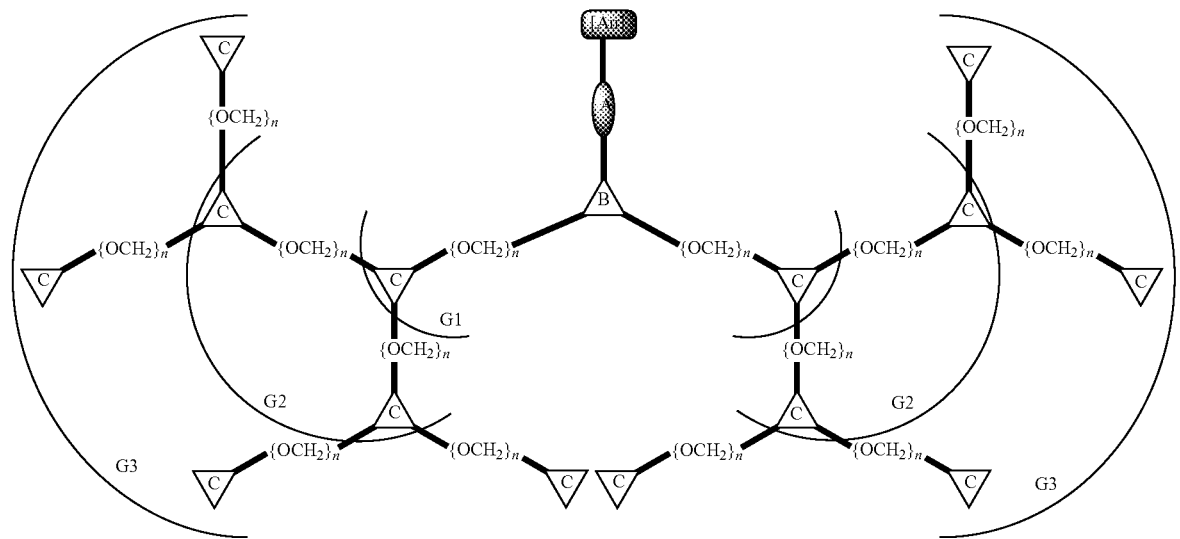

wherein:
(a) [Au] is a cyclometalated tridentate gold(III) group;
(b) Unit A is a σ-donating chemical group;
(c) Unit B is a central part of the dendrons comprising a branch point of component dendrimers;
(d) Unit C is optional surface groups or dendrons of the dendrimers;
(e) n=0 or 1.

Unit A is selected from, but is not limited to, alkylalkynyl, substituted alkylalkynyl, arylalkynyl, substituted arylalkynyl, heteroarylalkynyl and substituted heteroarylalkynyl.

Units B and C are benzene, phenyl derivatives, pyridine or pyridyl derivatives, or other related compounds, optionally with one or more alkyl, alkenyl, alkynyl, alkylaryl, cycloalkyl, OR, $NR_2$, SR, C(O)R, C(O)OR, $C(O)NR_2$, CN, $CF_3$, $NO_2$, $SO_2$, SOR, $SO_3R$, halo, aryl, substituted aryl, heteroaryl, substituted heteroaryl, heterocyclic group.

In the present disclosure the following terms are used.

The term "optional" or "optionally" means that the subsequently described event or circumstance may or may not occur, and that the description includes instances where said event or circumstance occurs and instances in which it does not. For example, "optionally substituted alkyl" includes "alkyl" and "substituted alkyl," as defined below.

The term "halo" or "halogen" as used herein includes fluorine, chlorine, bromine and iodine.

The term "alkyl" as used herein includes straight and branched chain alkyl groups, as well as cycloalkyl groups with alkyl groups having a cyclic structure. Preferred alkyl groups are those containing between one to eighteen carbon atoms and includes methyl, ethyl, propyl, isopropyl, butyl, isobutyl, tert-butyl, and other similar compounds. In addition, the alkyl group may be optionally substituted with one or more substituents selected from OR, NR$_2$, SR, C(O)R, C(O)OR, C(O)NR$_2$, CN, CF$_3$, NO$_2$, SO$_2$, SOR, SO$_3$R, halo and cyclic-amino.

The term "alkenyl" as used herein includes both straight and branched chain alkene radicals. Preferred alkenyl groups are those containing between two and eighteen carbon atoms. In addition, the alkenyl group may be optionally substituted with one or more substituents selected from OR, NR$_2$, SR, C(O)R, C(O)OR, C(O)NR$_2$, CN, CF$_3$, NO$_2$, SO$_2$, SOR, SO$_3$R, halo and cyclic-amino.

The term "alkynyl" as used herein includes both straight and branched chain alkyne radicals. Preferred alkynyl groups are those containing between two and eighteen carbon atoms. In addition, the alkynyl group may be optionally substituted with one or more substituents selected from OR, NR$_2$, SR, C(O)R, C(O)OR, C(O)NR$_2$, CN, CF$_3$, NO$_2$, SO$_2$, SOR, SO$_3$R, halo and cyclic-amino.

The term "arylalkynyl" as used herein includes an alkynyl group which has an aromatic group as a substituent. In addition, the arylalkynyl group may be optionally substituted with one or more substituents selected from OR, NR$_2$, SR, C(O)R, C(O)OR, C(O)NR$_2$, CN, CF$_3$, NO$_2$, SO$_2$, SOR, SO$_3$R, halo and cyclic-amino.

The term "alkylaryl" as used herein includes an alkyl group which has an aromatic group as a substituent. In addition, the alkylaryl group may be optionally substituted with one or more substituents selected from OR, NR$_2$, SR, C(O)R, C(O)OR, C(O)NR$_2$, CN, CF$_3$, NO$_2$, SO$_2$, SOR, SO$_3$R, halo and cyclic-amino.

Aryl alone or in combination includes carbocyclic aromatic systems. The systems may contain one, two or three rings wherein each ring may be attached together in a pendant manner or may be fused. Preferably the rings are 5- or 6-membered rings.

Heteroaryl alone or in combination includes heterocyclic aromatic systems. The systems may contain one, two or three rings wherein each ring may be attached together in a pendant manner or may be fused. Preferably the rings are 5- or 6-membered rings.

Heterocyclic and heterocycle refer to a 3 to 7-membered ring containing at least one heteroatom. This includes aromatic rings including but not limited to pyridine, thiophene, furan, pyrazole, imidazole, oxazole, isoxazole, thiazole, isothiazole, pyrrole, pyrazine, pyridazine, pyrimidine, benzimidazole, benzofuran, benzothiazole, indole, naphthalene, triazole, tetrazole, pyran, thiapyran, oxadiazole, triazine, tetrazine, carbazole, dibenzothiophene, dibenzofuran, fluorine, and non-aromatic rings including but not limited to piperazine, piperidine, and pyrrolidine. The groups of the present invention can be substituted or unsubstituted. Preferred substituents include but are not limited to alkyl, alkoxy, aryl.

Heteroatom refers to S, O, N, P.

Substituted refers to any level of substitution although mono-, di- and tri-substitutions are preferred. Preferred substituents include hydrogen, halogen, aryl, alkyl and heteroaryl.

Cyclometalated ligand is a term well known in the art and includes but is not limited to 2,6-diphenylpyridine (C^N^C), 2,6-bis(4-tert-butylphenyl)pyridine ($^t$BuC^N^C$^t$Bu), 2,6-diphenyl-4-(2,5-difluorophenyl)pyridine (2,5-F$_2$—C$_6$H$_3$—C^N^C), 2,6-diphenyl-4-p-tolylpyridine (C^NTol^C), 2,6-diphenyl-4-phenylpyridine (C^NPh^C), 2,6-bis(4-fluorophenyl)pyridine (FC^N^CF), 2,6-diphenyl-4-(4-isopropylphenyl)pyridine (4-$^i$Pr-Ph-C^N^C), 2,6-diphenyl-4-(4-nitrophenyl)pyridine (4-NO$_2$-Ph-C^N^C), 2,6-diphenyl-4-(4-methoxyphenyl)pyridine (4-OMe-Ph-C^N^C), 2,6-diphenyl-4-(4-methylphenyl)pyridine (4-Me-Ph-C^N^C), 2,6-diphenyl-4-(4-ethylphenyl)-pyridine (4-Et-Ph-C^N^C), 2,6-diphenyl-4-(2,3,4-trimethoxyphenyl)pyridine (2,3,4-OMe$_3$-Ph-C^N^C), 2,6-bis(4-methoxyphenyl)-4-(4-nitrophenyl)pyridine (4-NO$_2$-Ph-MeOC^N^COMe), 2,6-bis(2,4-dichlorophenyl)-4-(4-isopropylphenyl)-pyridine (4-$^i$Pr-Ph-Cl$_2$C^N^CCl$_2$), 2,6-diphenyl-4-(4-tosylphenyl)pyridine (4-OTs-Ph-C^N^C), 2,6-diphenyl-4-(4-dimethylaminophenyl)pyridine (4-NMe$_2$-Ph-C^N^C), 2,6-diphenyl-4-(4-diphenylaminophenyl)pyridine (4-NPh$_2$-Ph-C^N^C), 2,6-diphenyl-4-(4-bromophenyl)pyridine (4-Br-Ph-C^N^C), 2,6-diphenyl-4-(4-chlorophenyl)pyridine (4-Cl-Ph-C^N^C), 2,6-diphenyl-4-(4-fluorophenyl)pyridine (4-F-Ph-C^N^C), 2,6-diphenyl-4-(4-iodophenyl)pyridine (4-I-Ph-C^N^C), 2,6-diphenyl-4-(2,5-dimethylphenyl)pyridine (2,5-Me$_2$-Ph-C^N^C), 2,6-diphenyl-4-(2,3,4,5,6-pentafluorophenyl)pyridine (2,3,4,5,6-F$_5$-Ph-C^N^C), and 1,3-diphenylisoquinoline (dpiq).

Benzene includes substituted or unsubstituted benzene.
Pyridine includes substituted or unsubstituted pyridine.
Thiophene includes substituted or unsubstituted thiophene.
Furan includes substituted or unsubstituted furan.
Pyrazole includes substituted or unsubstituted pyrazole.
Imidazole includes substituted or unsubstituted imidazole.
Oxazole includes substituted or unsubstituted oxazole.
Isoxazole includes substituted or unsubstituted isoxazole.
Thiazole includes substituted or unsubstituted thiazole.
Isothiazole includes substituted or unsubstituted isothiazole.
Pyrrole includes substituted or unsubstituted pyrrole.
Pyrazine includes substituted or unsubstituted pyrazine.
Pyridazine includes substituted or unsubstituted pyridazine.
Pyrimidine includes substituted or unsubstituted pyrimidine.
Benzimidazole includes substituted or unsubstituted benzimidazole.
Benzofuran includes substituted or unsubstituted benzofuran.
Benzothiazole includes substituted or unsubstituted benzothiazole.
Indole includes substituted or unsubstituted indole.
Naphthalene includes substituted or unsubstituted naphthalene.
Triazole includes substituted or unsubstituted triazole.
Tetrazole includes substituted or unsubstituted tetrazole.
Pyran includes substituted or unsubstituted pyran.
Thiapyran includes substituted or unsubstituted thiapyran.
Oxadiazole includes substituted or unsubstituted oxadiazole.
Triazine includes substituted or unsubstituted triazine.
Tetrazine includes substituted or unsubstituted tetrazine.
Carbazole includes substituted or unsubstituted carbazole.
Dibenzothiophene includes substituted or unsubstituted dibenzothiophene.
Dibenzofuran includes substituted or unsubstituted dibenzofuran.
Piperazine includes substituted or unsubstituted piperazine.
Piperidine includes substituted or unsubstituted piperidine.
Pyrrolidine includes substituted or unsubstituted pyrrolidine.

In some embodiments of the invention, the luminescent gold(III) dendrimers of structure (I) are prepared in high purity. The compounds described have been represented throughout by their monomeric structure. As is well known to those in the art, the compounds may also be present as dimers, trimers or dendrimers.

The luminescent gold(III) dendrimers can be used to form thin films by spin-coating, ink-jet printing or other known fabrication methods and be applied in OLEDs. Referring to FIG. 1, an organic EL device has, in order, substrate 112, hole-injecting anode 110, hole transporting layer 108, light-emitting layer 106, electron transporting layer 104, and electron-injecting cathode 102.

Substrate 112 is electrically insulated and can be either optically transparent, and comprise glass, plastic foil, or other appropriate material, or alternatively, may be opaque and comprise one or more semiconducting materials or ceramics. In one embodiment of the invention, the EL emission is viewed through substrate 112, or through both sides of the device, and substrate 112 comprises a transparent glass substrate or a plastic foil. In other embodiments, the EL emission is viewed only through the top electrode, and substrate 112 comprises an opaque semiconductor or ceramic wafers. Hole-injecting anode 110 injects holes into the organic EL layer when anode 110 is positively biased. Anode 110 is composed of a conductive and optionally transmissive layer. In one embodiment of the invention, viewing the EL emission through the substrate is desirable, and hole-injecting anode 110 is transparent. In other embodiments, the EL emission is viewed through the top electrode and the transmissive characteristics of anode 110 are immaterial, and therefore any appropriate materials including metals or metal compounds having a work function of greater than 4.1 eV are used. Appropriate metals include gold, iridium, molybdenum, palladium, and platinum. In some embodiments anode 110 is transmissive, and suitable materials are metal oxides, including indium-tin oxide, aluminum- or indium-doped zinc oxide, tin oxide, magnesium-indium oxide, nickel-tungsten oxide, and cadmium-tin oxide. The preferred metals and metal oxides can be deposited by evaporation, sputtering, laser ablation, and chemical vapor deposition. Suitable materials for hole-transporting layer 108 include polycyclic aromatic compounds, for example, 4,4'-bis[N-(1-naphthyl)-N-phenylamino]biphenyl (NPB), 4,4'-bis[N-(3-methylphenyl)-N-phenylamino]biphenyl (TPD), 4,4',4''-tris[(3-methylphenyl)phenylamino]triphenylamine (MTDATA), and di-[4-(N,N-ditolyl-amino)phenyl]cyclohexane (TAPC). In addition, polymeric hole-transporting materials can be used including poly(N-vinylcarbazole) (PVK), polythiophene, polypyrrole, polyaniline, and copolymers including poly(3,4-ethylene-dioxythiophene):poly(4-styrene-surlfonate) (PEDOT:PSS).

Figure 2:
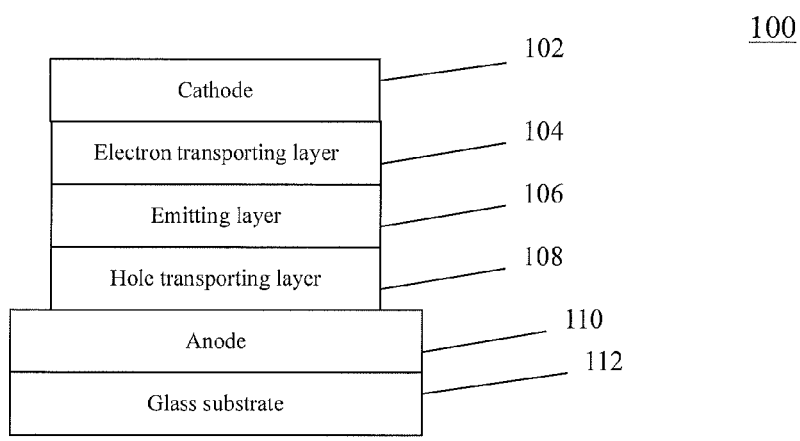
FIG. 2 is a schematic diagram of the basic structure of an organic EL device, in accordance with an embodiment of the present invention.

Light-emitting layer 106 in FIG. 2 is formed by doping the phosphorescent Au(III) metal complex as a dopant into a host compound. Suitable host materials should be selected so that the triplet exciton can be transferred efficiently from the host material to the phosphorescent dopant material. Suitable host materials include certain aryl amines, triazoles and carbazole compounds. Examples of desirable hosts are 4,4'-bis(carbazol-9-yl)biphenyl (CBP), m-(N,N'-dicarbazole)benzene (mCP), 4,4',4''-tris(carbazol-9-yl)triphenylamine (TCTA), 3-(4-biphenylyl)-4-phenyl-5-tert-butylphenyl-1,2,butylphenyl-1,2,4-triazole (TAZ), p-bis(triphenylsilyl)benzene (UGH2), and PVK.

Electron-transporting layer 104 consists of materials or mixtures of materials having a high ionization potential and wide optical band gap. Suitable electron-transporting materials include 1,3,5-tris(phenyl-2-benzimidazolyl)-benzene (TPBI), 1,3,5-tri[(3-pyridyl)-phen-3-yl]benzene (TMPyPB), bathocuproine (BCP), bathophenanthroline (BPhen) and bis(2-methyl-8-quinolinolate)-4-(phenylphenolate)aluminum (BAlq), tris-[2,4,6-trimethyl-3-(pyridin-3-yl)phenyl]borane (3TPYMB), 1,3,5-tri[(3-pyridyl)-phen-3-yl]benzene (TmPyPB), and 1,3-bis[3,5-di(pyridin-3-yl)phenyl]benzene (BmPyPhB). In one embodiment of the invention, electron transporting layer 104 is prepared as an organic film by thermal evaporation, spin-coating, ink-jet printing from a solution, or other known fabrication methods. Electron-injecting cathode 102 acts as a transmissive electron injector that injects electrons into the organic EL layer of anode 110 when cathode 102 is negatively biased. Cathode 102 comprises a thin fluoride layer (which may be omitted) and a metal or metal alloy, preferably having a work function of less than 4 eV. Suitable materials include Mg:Ag, Ca, Li:Al, Al.

In some embodiments of the invention, novel luminescent gold(III) dendrimers are either the primary luminescent material or a secondary luminescent material in device 100. In some embodiments the novel gold(III) dendrimers are employed as electrophosphorescent dopants in multilayer OLED with an EQE of up to 7.6%. Advantageously, the novel gold(III) compounds can be deposited in the OLEDs by spin-coating, screen printing or ink-jet printing. In addition, the modular molecular design of dendrimers as shown in Formula (I) allows independent optimization of electronic and processing properties combined with different metal centres producing OLEDs having various emission colours. The high solubility of the luminescent gold(III) dendrimers in a variety of organic solvents permits simple and economic manufacturing and patterning of large-area displays.

In general, emissive layer 106 is sandwiched between hole-transporting layer 108 and electron-transporting layer 104. To ensure an efficient exothermic energy transfer between the host material and the dopant material, the triplet energy of the host material must be larger than that of the dopant material. In addition, both the ionization potential and the electron affinity of the host material should be larger than those of the dopant material in order to achieve efficient Foster energy transfer from the host to the dopant. In order to confine triplet excitons within emissive layer 106, the triplet energy of hole-transporting material 102 and electron-transporting material 104 should be larger than that of the dopant material.

The present invention will be illustrated more specifically by the following non-limiting examples, it being understood that changes and variations can be made therein without deviating from the scope and the spirit of the invention as hereinafter claimed. It is also understood that various theories as to why the invention works are not intended to be limiting.

Example 1

Synthesis and Characterization of Ligands 1-10

1-(3,5-dimethoxybenzyl)-4-(4-ethynylphenyl)-1H-1,2,3-triazole (ligand L1), 1-(3,5-bis-(3,5-dimeoxybenzyloxy)benzyl)-4-(4-ethynylphenyl)-1H-1,2,3-triazole (ligand L2), and 1-(3,5-bis(3,5-bis(3,5-di methoxybenzyloxy)benzyloxy)benzyl)-4-(4-ethylphenyl)-1H-1,2,3-triazole (ligand L3) were synthesized according to the following methodology. 3,5-dimethoxybenzylazide (precursor P1), 3,5-bis(3,5-dimethoxybenzyloxy)benzylazide (precursor P2), and [3,5-bis(3,5-bis(3,5-dimethoxybeenzyloxy)benzyloxy)]benzylazide (precursor P3) were synthesized according to the published procedure [Lee, J. W.; Kim, B. K.; Kim, J. H.; Shin, W. S.; Jin, S. H. Bull. Korean Chem. Soc, 26, 1790 (2005)]. For example, 3,5-dimethoxybenzyl bromide (1.50 g, 6.50 mmol) and sodium azide (1.27 g, 20.50 mmol) were dissolved in DMF (30 mL) and heated in a sealed glass vessel under reflux for 12 h. The crude product was obtained by removal of solvent from the reaction mixture. The crude product was dissolved in dichloromethane (15 mL) and recrystallized by diffusion of pentane vapor into the solution. to give ligand precursor P1 as a pale white solid (1.20 g).

Ligand precursors P2 and P3 were similarly synthesized.

Next, target ligands were synthesized from their respective precursors by the reaction of different polyarylether azide ligands with 1,4-diethynylbenzene in the presence of a catalytic amount of sodium ascorbate and $CuSO_4 \cdot 5H_2O$. For example, a mixture of 1,4-diethynylbenzene (0.15 g, 0.75 mmol) and precursor P1 (0.13 g, 0.90 mmol) in the presence of 5 mol % $CuSO_4 \cdot 5H_2O$ (7.50 mg, 0.03 mmol) with 5 mol % sodium ascorbate (11.88 mg, 0.06 mmol) were dissolved in degassed (8 mL) DMF and $H_2O$ (2 mL) and stirred for twelve hours under a nitrogen atmosphere at 50-60° C. The crude product was cooled to room temperature and then extracted with diethyl ether (20 mL). The desired product was isolated by column chromatography using ethyl acetate as the eluent. Column fractions were combined, the solvent removed, and subsequent recrystallization by diffusion of pentane vapor into a solution of the product in dichloromethane (10 mL) gave ligand L1 as a pale white solid. The yield of the ligand was approximately 70%.

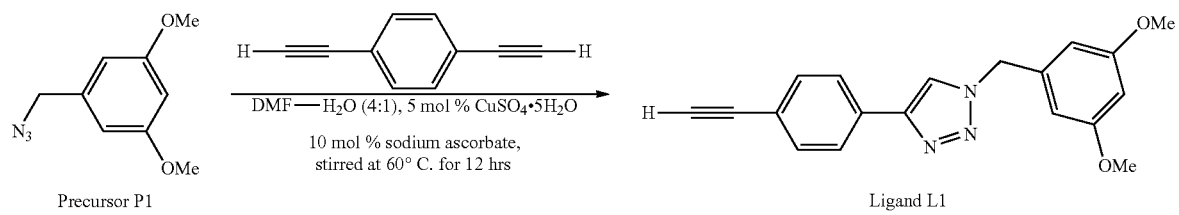

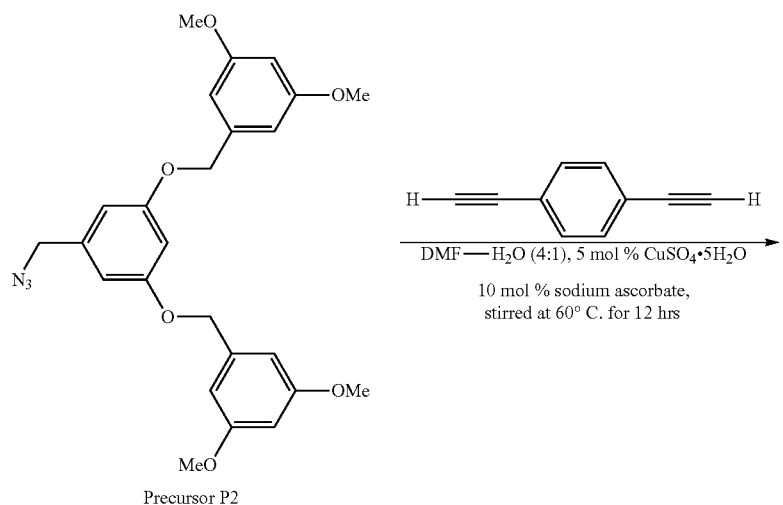

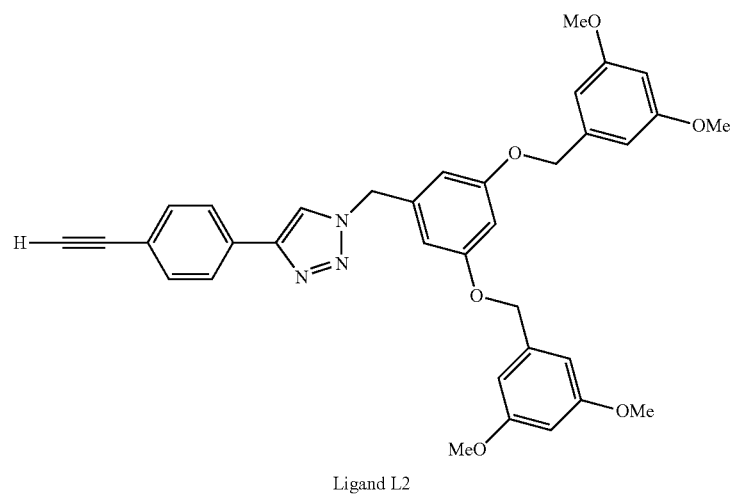

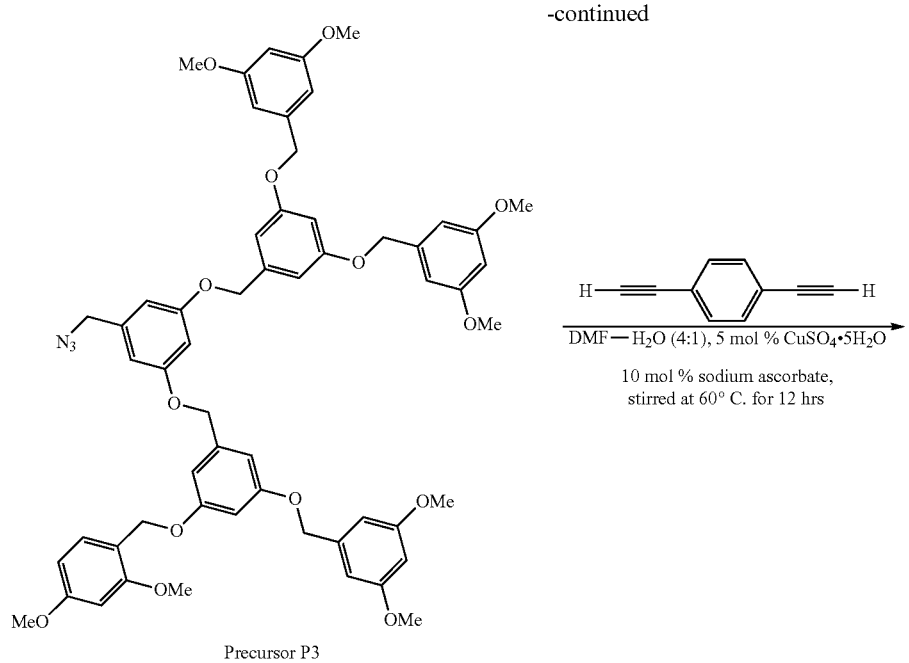

Precursor P3

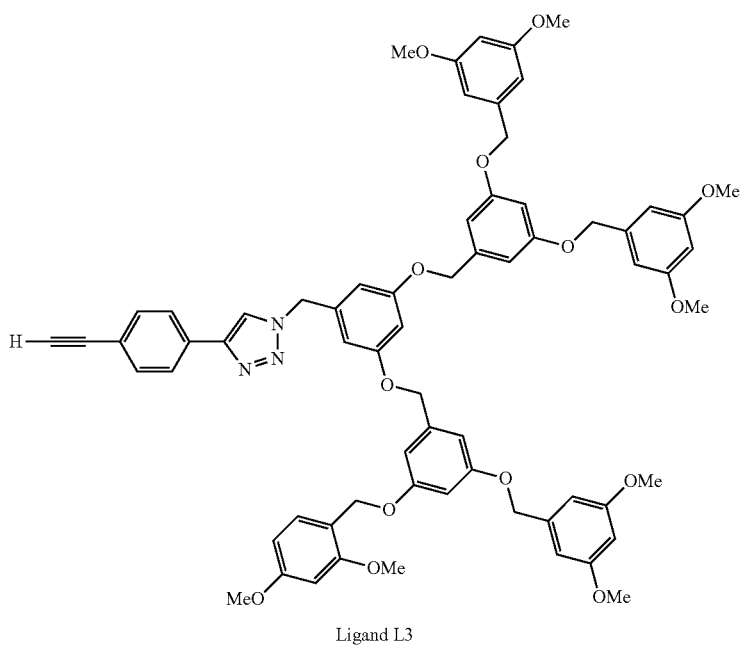

Ligand L3

Carbazole or triphenylamine based dendritic alkynye ligands L4-L10 were synthesized according to the following methodology. The protected forms, precursors P4-P10, were prepared according to a modification of a procedure reported in the literature [Liu, Q. D.; Lu, J. P.; Day, M.; Tao, Ye.; Barrios, P.; Stupak, J.; Chan, K.; Li, J. J.; Chi, Y. *Adv. Funct. Mater.* 17, 1028, (2007); Kikuchi, A.; Nose, T. *Macromolecules* 30, 892 (1997); Zhu, M. R.; Zou, J. H.; Hu, S. J.; Li, C.; Yang, C. L.; Wu, H. B.; Qin, J. Q.; Cao, Y. *J. Mater. Chem.* 22, 361 (2012)]. Each target ligand was obtained by de-protection of the corresponding precursor ligand in a mixture of $K_2CO_3$ or tetrabutylammonium fluoride (TBAF) and an organic solvent. For example, a mixture of precursor P4 and $K_2CO_3$ in THF and MeOH was stirred for four hours under a nitrogen atmosphere at room temperature. The solvents were removed under reduced pressure. The crude product was diluted with dichloromethane. The organic phase was washed with NaCl in water three times (20 mL×3), and then extracted three times with dichloromethane (20 mL×3). The organic extract was dried over anhydrous $Na_2SO_4$ and filtered to remove $Na_2SO_4$. The solvent (dichloromethane) was evaporated under reduced pressure. Further purification was accomplished by column chromatography on silica gel with hexane-dichloromethane (6:1, v/v) as the eluent. The elution process was monitored by thin layer chromatography (TLC). Column fractions containing the product ($R_f$=0.42) were pooled and the solvent removed by evaporation under reduced pressure. Subsequent recrystallization by diffusion of diethyl ether vapor into the solution of the product in dichloromethane gave ligand L4 as a pale brown solid.

Ligands L5-L10 were synthesized from precursors P5-P10 using the same procedure.
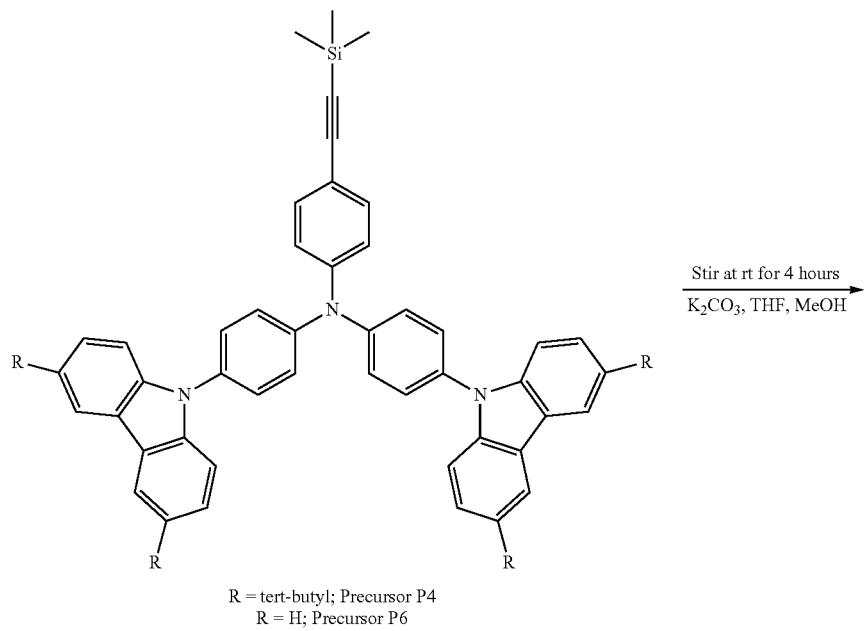
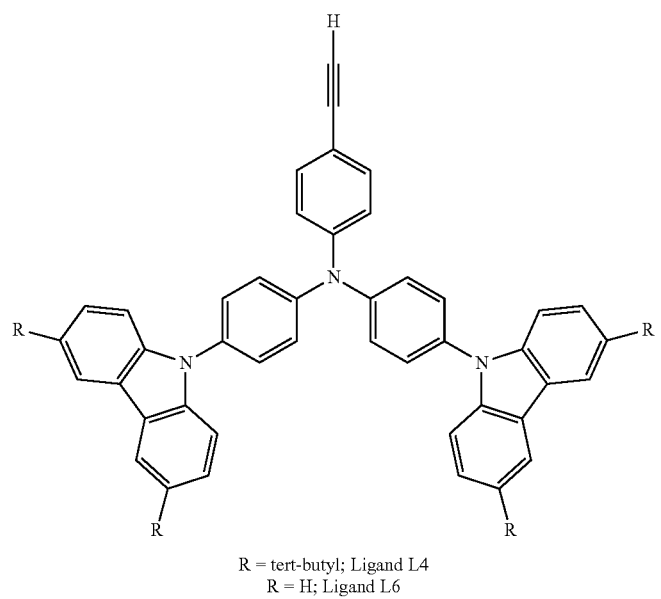

-continued
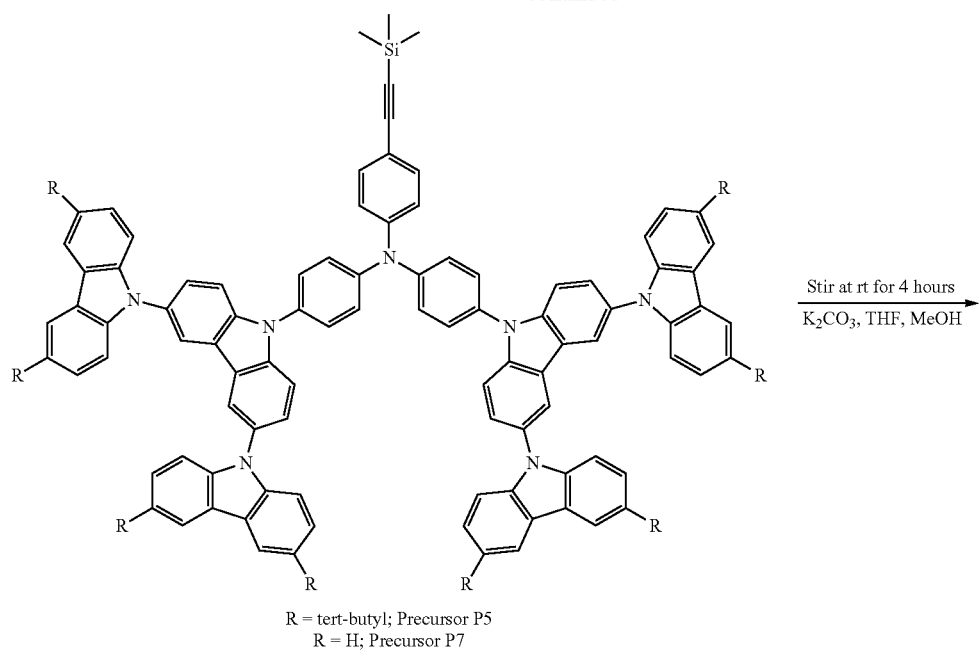
R = tert-butyl; Precursor P5
R = H; Precursor P7
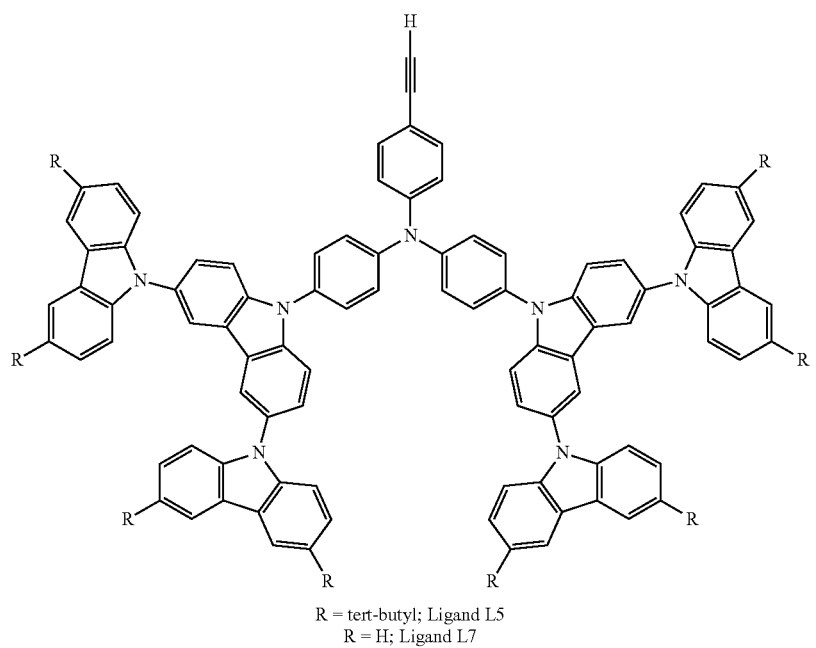
R = tert-butyl; Ligand L5
R = H; Ligand L7

-continued
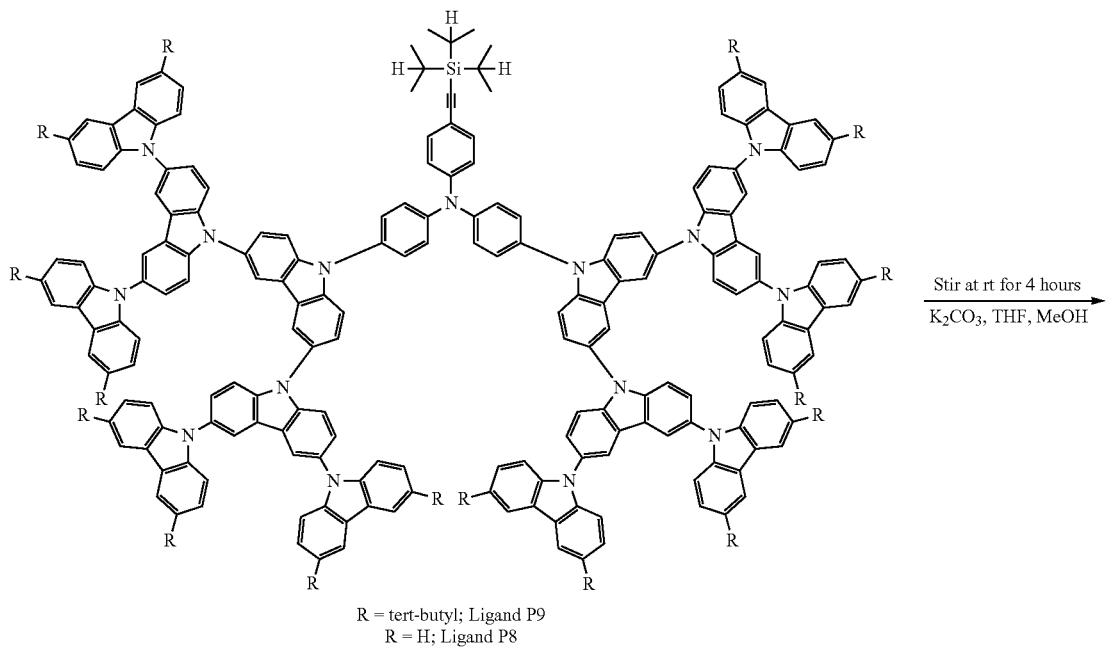
R = tert-butyl; Ligand P9
R = H; Ligand P8
Stir at rt for 4 hours
K₂CO₃, THF, MeOH
→
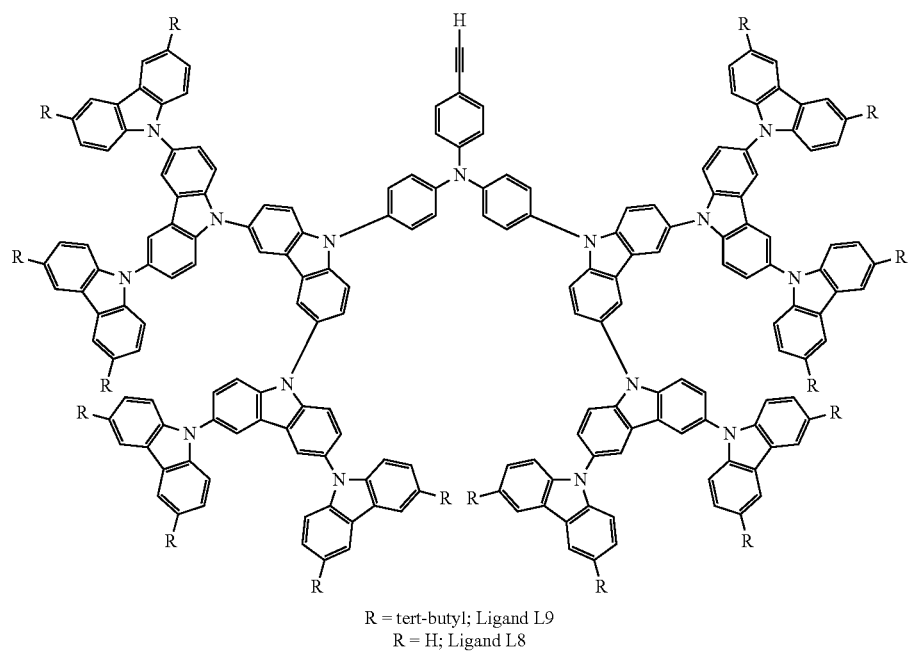
R = tert-butyl; Ligand L9
R = H; Ligand L8

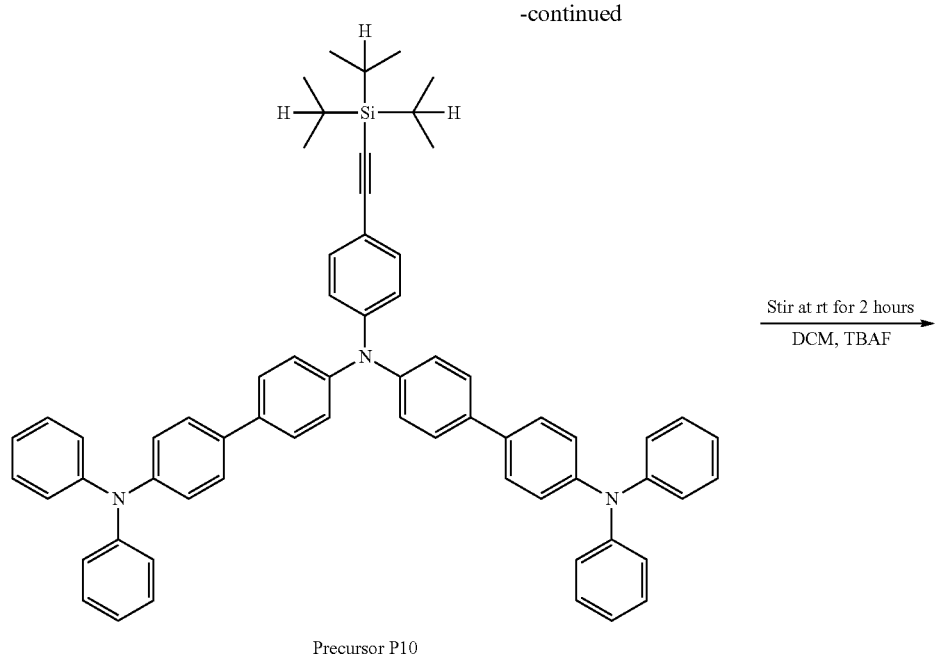

Precursor P10

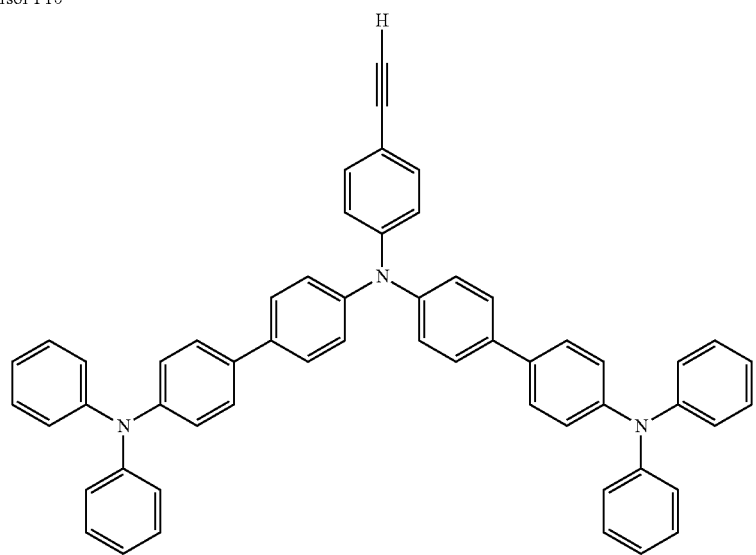

Ligand L10

Example 2

Synthesis and Characterization of Gold(III) Dendrimers

Compounds 1-13 were synthesized according to the following methodology.

The tridentate ligands, 2,5-$F_2$—$C_6H_3$—C^N^C, BuC-^N^CBu, dpiq, and the precursor compounds, [Au(C^N^C)Cl], [Au(2,5-$F_2$—$C_6H_3$—C^N^C)Cl)], [Au($^t$BuC^N^C$^t$Bu)Cl] and [Au(dpiq)Cl], respectively, were prepared according to a modification of a procedure reported in the literature [Krohnke, F. *Synthesis* 1 (1976); Wong, K. H.; Cheung, K. K.; Chan, M. C. W.; Che, C. M. *Organometallics*, 17, 5305 (1998)].

The target compounds were synthesized by the reaction of the respective [Au(C^N^C)Cl], [Au(2,5-$F_2$—$C_6H_3$—C^N^C) Cl), [Au($^t$BuC^N^C$^t$Bu)Cl] and [Au(dpiq)Cl] with different alkynes in the presence of a catalytic amount of copper(I) iodide in base and organic solvent. For example, compound 1 was synthesized from a mixture of [Au(2,5-$F_2$—$C_6H_3$—C^N^C)Cl] (1.04 g, 0.18 mmol), copper(I) iodide (3.80 mg, 0.02 mmol), triethylamine (2 mL) and ligand L1 (0.60 g, 0.18 mmol) in degassed dichloromethane solution (30 mL) for twelve hours under a nitrogen atmosphere at room temperature. After removing the solvent, the crude product was purified by column chromatography on silica gel using ethyl acetate as the eluent. Column fractions containing the product were combined and evaporated to dryness under reduced pressure. The residue was dissolved in dichloromethane. Subsequent recrystallization by diffusion of diethyl ether vapor into the dichloromethane solution of the product (35 mL) gave compound 1 (40 mg) as pale yellow crystals. Compounds 2 through 13 were synthesized from their respective precursors using similar procedures.

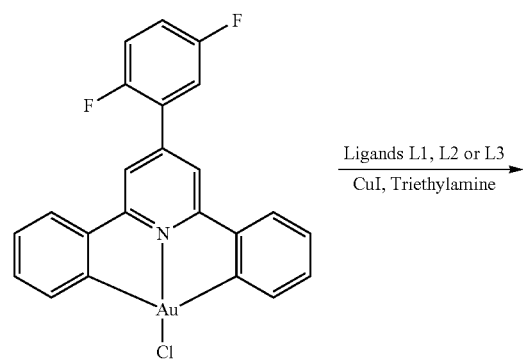
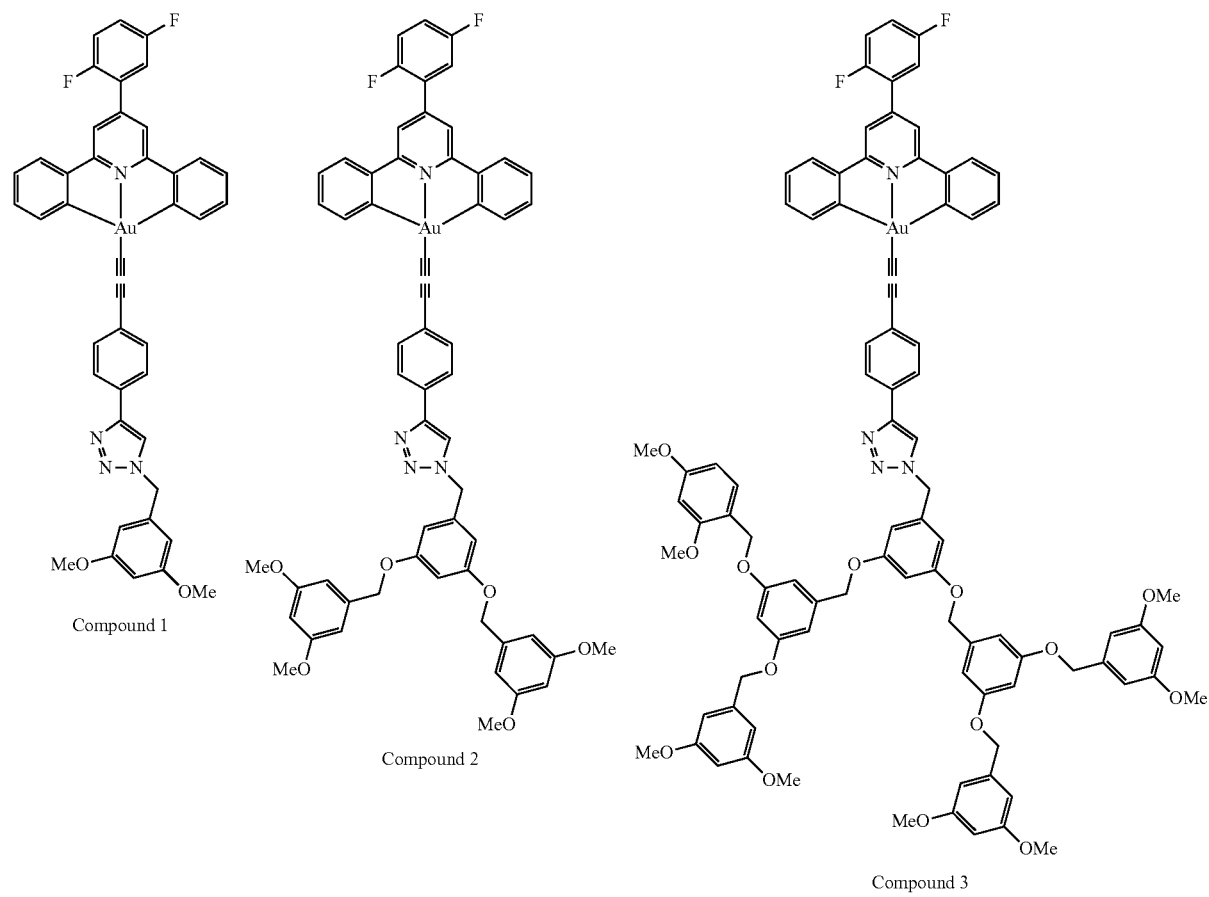
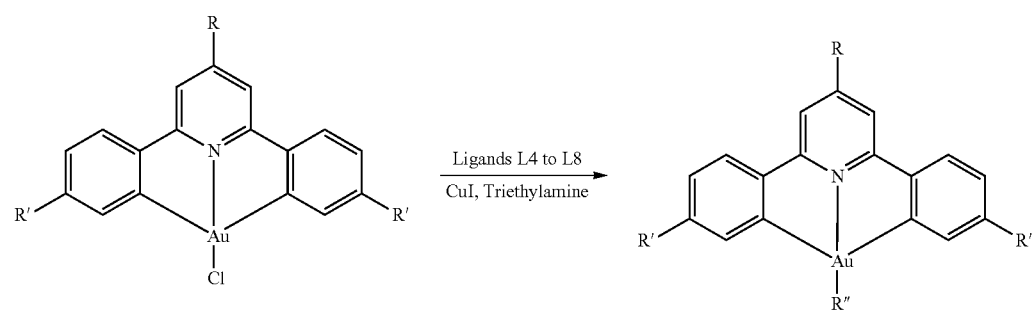

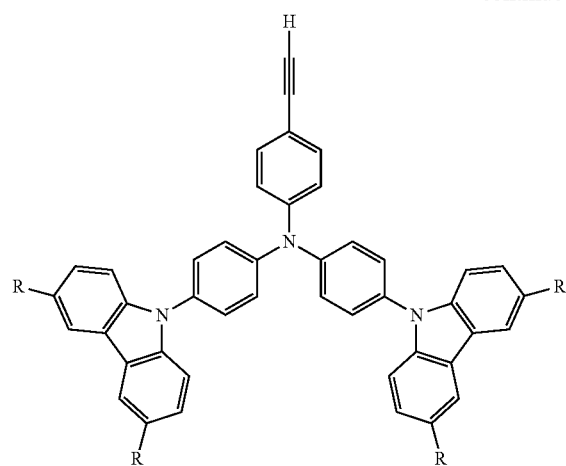
R = tert-butyl group; Ligand L4
R = H; Ligand L6
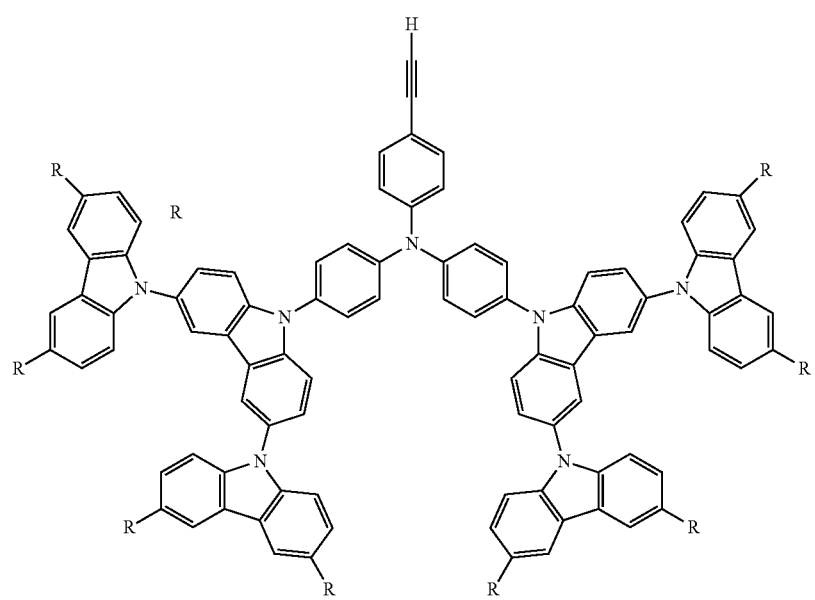
R = tert-butyl group; Ligand L5
R = H; Ligand L7

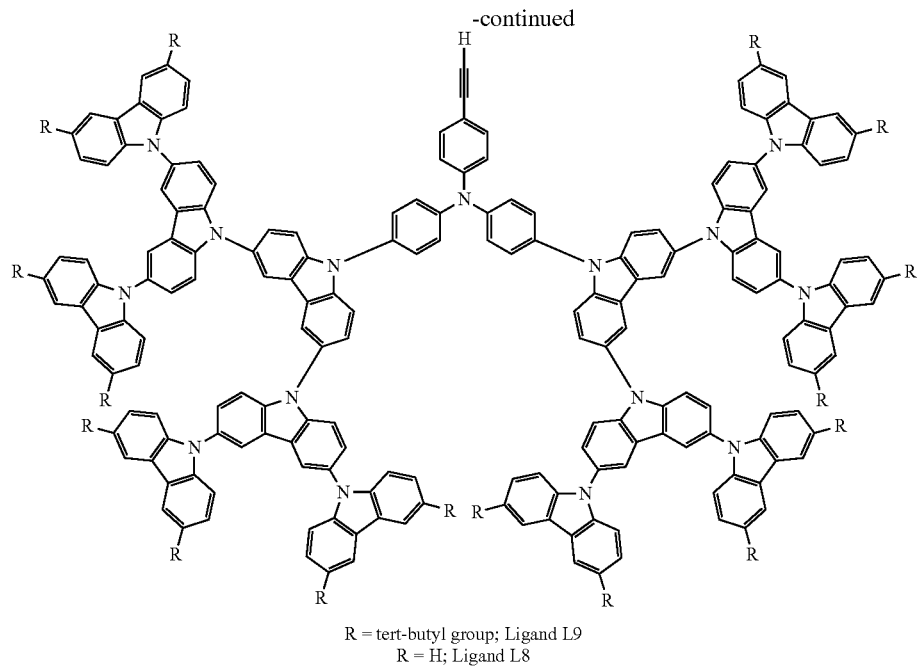

R = tert-butyl group; Ligand L9
R = H; Ligand L8

R = 2,5-F$_2$C$_6$H$_3$; R$_2$ = H; R″ = Ligand L4 (Compound 4)
R = 2,5-F$_2$C$_6$H$_3$; R$_2$ = H; R″ = Ligand L5 (Compound 5)
R = H; R′ = tert-butyl group; R″ = Ligand L6 (Compound 6)
R = H; R′ = tert-butyl group; R″ = Ligand L7 (Compound 7)
R = H; R′ = tert-butyl group; R″ = Ligand L8 (Compound 8)
R = H; R′ = tert-butyl group; R″ = Ligand L4 (Compound 9)
R = H; R′ = H; R″ = Ligand L4 (Compound 10)
R = 2,5-F$_2$C$_6$H$_3$; R$_2$ = H; R″ = Ligand L9 (Compound 11)

$^1$H NMR spectra were recorded on a Bruker AVANCE 400 (400 MHz) Fourier-transform NMR spectrometer with chemical shifts reported relative to tetramethylsilane. Positive FAB mass spectra were recorded on a Thermo Scientific DFS High Resolution Magnetic Sector Mass Spectrometer. IR spectra were recorded using a KBr disk on a Bio-Rad FTS-7 FTIR spectrometer (4000-400 cm$^{-1}$). Elemental analyses for the metal complexes were performed on the Carlo Erba 1106 elemental analyzer at the Institute of Chemistry, Chinese Academy of Sciences in Beijing. The results of the analyses confirm the high purity of all compounds 1-13.

The characteristic spectral properties of ligands L1-L10 and compounds 1-13 are as follows:

Ligand L1: Yield: 170 mg, 70%. $^1$H NMR (400 MHz, DMSO-d$_6$, 298 K, relative to Me$_4$Si): δ 3.11 (s, 1H), 3.71 (s, 6H), 5.55 (s, 2H), 6.47 (t, J=2.0 Hz, 1H), 6.51 (d, J=2.0 Hz, 2H), 7.54 (d, J=8.4 Hz, 2H), 7.87 (d, J=8.4 Hz, 2H), 8.67 (s, 1H). Positive FAB-MS: m/z 319 [M]$^+$. Elemental analyses: Found (%): C, 71.34; H, 5.55; N, 13.11. Calcd for C$_{19}$H$_{17}$N$_3$O$_2$: C, 71.45; H, 5.36; N, 13.15.

Ligand L2: Yield: 230 mg, 78%. $^1$H NMR (400 MHz, DMSO-d$_6$, 298 K, relative to Me$_4$Si): δ 3.11 (s, 1H), 3.71 (s, 12H), 5.00 (s, 4H), 5.55 (s, 2H), 6.47 (t, J=2.0 Hz, 2H), 6.56-6.62 (m, 7H), 7.54 (d, J=11.1 Hz, 2H), 7.85 (d, J=11.1 Hz, 2H), 8.65 (s, 1H). Positive FAB-MS: m/z 592 [M]$^+$. Elemental analyses: Found (%): C, 68.91; H, 5.97; N, 6.67. Calcd for C$_{35}$H$_{33}$N$_3$O$_6$.H$_2$O: C, 68.95; H, 5.78; N, 6.89.

Ligand L3: Yield: 175 mg, 78%. $^1$H NMR (400 MHz, DMSO-d$_6$, 298 K, relative to Me$_4$Si): δ 3.11 (s, 1H), 3.71 (s, 24H), 4.96 (s, 12H), 5.53 (s, 2H), 6.41 (t, J=2.0 Hz, 2H), 6.56-6.68 (m, 19H), 7.50 (d, J=8.4 Hz, 2H), 7.83 (d, J=8.4 Hz, 2H), 8.61 (s, 1H). Positive FAB-MS: m/z 1137 [M]$^+$. Elemental analyses: Found (%): C, 70.51; H, 5.81; N, 3.44. Calcd for C$_{67}$H$_{65}$N$_3$O$_{14}$.1/2H$_2$O: C, 70.27; H, 5.81; N, 3.67.

Ligand L4: Yield: 480 mg, 83%. $^1$H NMR (400 MHz, CDCl$_3$, 298 K, relative to Me$_4$Si): δ 1.47 (s, 36H), 3.08 (s, 1H), 7.36-7.42 (m, 10H), 7.46-7.52 (m, 10H), 8.14 (d, J=2.0 Hz, 4H). Positive FAB-MS: m/z 823 [M]$^+$. Elemental analyses: Found (%): C, 86.76; H, 7.21; N, 4.97. Calcd for C$_{60}$H$_{61}$N$_3$.1/2H$_2$O: C, 86.49; H, 7.50; N, 5.04.

Ligand L5: Yield: 200 mg, 83%. $^1$H NMR (400 MHz, CDCl$_3$, 298 K, relative to Me$_4$Si): δ 1.57 (s, 72H), 3.11 (s, 1H), 7.30-7.67 (m, 18H), 7.72-7.75 (m, 18H), 8.18 (d, J=1.5 Hz, 8H), 8.28 (d, J=1.8 Hz, 4H). Positive FAB-MS: m/z 1707 [M]$^+$. Elemental analyses: Found (%): C, 85.19; H, 7.36; N, 5.54. Calcd for C$_{124}$H$_{121}$N$_7$.2H$_2$O: C, 85.33; H, 7.21; N, 5.61.

Ligand L6: Yield: 230 mg, 77%. $^1$H NMR (400 MHz, CD$_2$Cl$_2$, 298 K, relative to Me$_4$Si): δ 3.15 (s, 1H), 7.26 (d, J=8.4 Hz, 2H), 7.29-7.33 (m, 4H), 7.44-7.57 (m, 18H), 8.17 (d, J=8.0 Hz, 4H). Positive FAB-MS: m/z 599 [M]$^+$. Elemental analyses: Found (%): C, 87.07; H, 4.98; N, 6.99. Calcd for C$_{44}$H$_{29}$N$_3$.1/2H$_2$O: C, 86.81; H, 4.96; N, 6.90.

Ligand L7: Yield: 210 mg, 80%. $^1$H NMR (400 MHz, CDCl$_3$, 298 K, relative to Me$_4$Si): δ 3.12 (s, 1H), 7.17 (d, J=11.6 Hz, 2H), 7.27-7.33 (m, 8H), 7.40 (d, J=6.0 Hz, 16H), 7.54 (d, J=11.6 Hz, 4H), 7.65 (dd, J=11.6 and 2.4 Hz, 4H), 7.69-7.77 (m, 10H), 8.17 (d, J=11.6 Hz, 8H), 8.30 (d, J=2.2 Hz, 4H). Positive FAB-MS: m/z 1260 [M]$^+$. Elemental analyses: Found (%): C, 87.38; H, 4.50; N, 7.54. Calcd for C$_{92}$H$_{57}$N$_7$: C, 87.66; H, 4.56; N, 7.77.

Ligand L8: Yield: 60 mg, 77%. $^1$H NMR (400 MHz, CDCl$_3$, 298 K, relative to Me$_4$Si): δ 3.15 (s, 1H), 7.21-7.31 (m, 16H), 7.34-7.40 (m, 34H), 7.56-7.77 (m, 22H), 7.81 (dd, J=7.3 and 1.0 Hz, 4H), 7.90 (d, J=8.4 Hz, 8H), 8.15 (d, J=7.8 Hz, 16H), 8.29 (d, J=8.4 Hz, 8H), 8.56 (d, J=2.0 Hz, 4H).

Positive FAB-MS: m/z 2579 [M]$^+$. Elemental analyses: Found (%): C, 85.86; H, 5.03; N, 7.81. Calcd for C$_{188}$H$_{113}$N$_{15}$·2½CH$_3$CH$_2$OCH$_2$CH$_3$: C, 85.93; H, 5.02; N, 7.59.

Ligand L9: Yield: 150 mg, 90%. $^1$H NMR (400 MHz, CDCl$_3$, 298 K, relative to Me$_4$Si): δ 1.40 (s, 144H), 3.15 (s, 1H,), 7.42 (d, J=8.8 Hz, 16H), 7.43-7.45 (m, 18H), 7.59-7.63 (m, 22H), 7.64 (d, J=8.8 Hz, 4H), 7.87-7.89 (m, 8H), 8.14 (d, J=1.8 Hz, 16H), 8.26 (d, J=1.8 Hz, 8H), 8.56 (s, 4H). Positive FAB-MS: m/z 3479 [M]$^+$. Elemental analyses: Found (%): C, 85.45; H, 7.51; N, 5.60. Calcd for C$_{252}$H$_{241}$N$_{15}$·3CH$_3$CH$_2$OCH$_2$CH$_3$: C, 85.65; H, 7.37; N, 5.67.

Ligand L10: Yield: 110 mg, 65%. $^1$H NMR (300 MHz, DMSO-d$_6$, 298 K, relative to Me$_4$Si): δ 3.04 (s, 1H), 7.04-7.11 (m, 18H), 7.18 (d, J=9.0 Hz, 4H), 7.29-7.34 (m, 8H), 7.41 (d, J=9.0 Hz, 2H), 7.59-7.66 (m, 8H). Positive FAB-MS: m/z 756 [M]$^+$.

Compound 1: [Au(2,5-F$_2$—C$_6$H$_3$—C^N^C-ligand L1)]. Yield: 40 mg, 27%. $^1$H NMR (400 MHz, DMSO-d$_6$, 298 K, relative to Me$_4$Si): δ 3.71 (s, 6H), 5.55 (s, 2H), 6.47 (d, J=2.0 Hz, 1H), 6.51 (t, J=2.0 Hz, 2H), 7.34 (dt, J=7.4 and 1.0 Hz, 2H), 7.44 (dt, J=7.4 and 1.0 Hz, 2H), 7.48-7.56 (m, 2H), 7.58 (d, J=8.2 Hz, 2H), 7.74-7.82 (m, 1H), 7.86 (d, J=7.4 Hz, 2H), 7.95 (dd, J=7.4 and 1.0 Hz, 2H) 8.02 (d, J=8.2 Hz, 2H), 8.18 (s, 2H), 8.67 (s, 1H). Positive FAB-MS: m/z 856 [M]$^+$. IR (KBr disk): 2150 cm$^{-1}$ ν(C≡C). Elemental analyses: Found (%): C, 58.33; H, 3.54; N, 6.43. Calcd for C$_{42}$H$_{29}$F$_2$N$_4$O$_2$Au·½H$_2$O: C, 58.27; H, 3.49; N, 6.47.

Compound 2: [Au(2,5-F$_2$—C$_6$H$_3$—C^N^C-ligand L2)]. Yield: 40 mg, 35%. $^1$H NMR (400 MHz, DMSO-d$_6$, 298 K, relative to Me$_4$Si): δ 3.70 (s, 12H), 5.00 (s, 4H), 5.55 (s, 2H), 6.41 (t, J=4.4 Hz, 2H), 6.56-6.64 (m, 7H), 7.34 (dt, J=7.6 and 1.0 Hz, 2H), 7.44 (dt, J=7.6 and 1.0 Hz, 2H), 7.48-7.55 (m, 2H), 7.58 (d, J=8.0 Hz, 2H), 7.77-7.81 (m, 1H), 7.82 (d, J=7.6 Hz, 2H), 7.94 (dd, J=7.6 and 1.0 Hz, 2H), 8.02 (d, J=8.0 Hz, 2H), 8.18 (s, 2H), 8.65 (s, 1H). Positive FAB-MS: m/z 1128 [M]$^+$. IR (KBr disk): 2146 cm$^{-1}$ ν(C≡C). Elemental analyses: Found (%): C, 61.26; H, 4.08; N, 4.88. Calcd for C$_{58}$H$_{45}$F$_2$N$_4$O$_6$Au·½H$_2$O: C, 61.21; H, 4.07; N, 4.92.

Compound 3: [Au(2,5-F$_2$—C$_6$H$_3$—C^N^C-ligand L3)]. Yield: 57 mg, 26%. $^1$H NMR (400 MHz, DMSO-d$_6$, 298 K, relative to Me$_4$Si): δ 3.70 (s, 24H), 5.00 (s, 12H), 5.54 (s, 2H), 6.41 (t, J=2.0 Hz, 2H), 6.56-6.66 (m, 19H), 7.33 (dt, J=8.0 and 1.0 Hz, 2H), 7.43 (dt, J=8.0 and 1.0 Hz, 2H), 7.48-7.55 (m, 2H), 7.56 (d, J=8.4 Hz, 2H), 7.77-7.82 (m, 1H), 7.84 (d, J=8.0 Hz, 2H), 7.93 (dd, J=8.0 and 1.0 Hz, 2H) 8.03 (d, J=8.4 Hz, 2H), 8.18 (s, 2H), 8.61 (s, 1H). Positive FAB-MS: m/z 1672 [M]$^+$. IR (KBr disk): 2150 cm$^{-1}$ ν(C≡C). Elemental analyses: Found (%): C, 64.76; H, 4.75; N, 3.51. Calcd for C$_{90}$H$_{77}$F$_2$N$_4$O$_{14}$Au: C, 64.59; H, 4.63; N, 3.34.

Compound 4: [Au(2,5-F$_2$—C$_6$H$_3$—C^N^C-ligand L4)]. Yield: 80 mg, 68%. $^1$H NMR (500 MHz, CD$_2$Cl$_2$, 298 K, relative to Me$_4$Si): δ 1.47 (s, 36H), 7.25-7.37 (m, 7H), 7.43-7.47 (m, 10H), 7.50-7.53 (m, 8H), 7.61 (d, J=4.8 Hz, 2H), 7.62-7.70 (m, 4H), 8.11 (dd, J=7.3 and 1.0 Hz, 2H) 8.16 (d, J=1.6 Hz, 4H). Positive FAB-MS: m/z 1360 [M]$^+$. IR (KBr disk): 2148 cm$^{-1}$ Elemental analyses: Found (%): C, 73.12; H, 5.54; N, 4.02. Calcd for C$_{83}$H$_{73}$F$_2$N$_4$Au: C, 73.22; H, 5.40; N, 4.11.

Compound 5: [Au(2,5-F$_2$—C$_6$H$_3$—C^N^C-ligand L5)]. Yield: 48 mg, 28%. $^1$H NMR (400 MHz, CDCl$_3$, 298 K, relative to Me$_4$Si): δ 1.46 (s, 72H), 7.20-7.25 (m, 3H), 7.27-7.39 (m, 12H), 7.44-7.47 (m, 10H), 7.58 (d, J=8.0 Hz, 4H), 7.67-7.75 (m, 18H), 8.16-8.18 (m, 10H), 8.25 (d, J=4.0 Hz, 4H). Positive FAB-MS: m/z 2242 [M]$^+$. IR (KBr disk): 2150 cm$^{-1}$ ν(C≡C). Elemental analyses: Found (%): C, 77.10; H, 6.07; N, 5.18. Calcd for C$_{147}$H$_{133}$F$_2$N$_8$Au·2H$_2$O: C, 77.34; H, 6.05; N, 4.91.

Compound 6: [Au($^t$BuC^N^C$^t$Bu-ligand L6)]. Yield: 48 mg, 45%. $^1$H NMR (500 MHz, CD$_2$Cl$_2$, 298 K, relative to Me$_4$Si): δ 1.26 (s, 18H), 7.28-7.34 (m, 8H), 7.43-7.58 (m, 18H), 7.62 (d, J=2.0 Hz, 2H), 7.63 (d, J=2.0 Hz, 2H), 7.87 (t, J=8.0 Hz, 1H), 8.16 (d, J=7.4 Hz, 4H), 8.21 (d, J=2.4 Hz, 2H). Positive FAB-MS: m/z 1136 [M]$^+$. IR (KBr disk): 2144 cm$^{-1}$ ν(C≡C). Elemental analyses: Found (%): C, 72.04; H, 4.96; N, 4.94. Calcd for C$_{69}$H$_{55}$N$_4$Au·H$_2$O: C, 71.74; H, 4.97; N, 4.85.

Compound 7: [Au($^t$BuC^N^CBu-ligand L7)]. Yield: 50 mg, 32%. $^1$H NMR (500 MHz, CD$_2$Cl$_2$, 298 K, relative to Me$_4$Si): δ 1.26 (s, 18H), 7.26-7.32 (m, 8H), 7.33 (dd, J=8.0 and 2.0 Hz, 2H), 7.39-7.43 (m, 18H), 7.48 (d, J=7.4 Hz, 2H), 7.58 (d, J=8.0 Hz, 2H), 7.63 (d, J=8.2 Hz, 4H), 7.66-7.69 (m, 6H), 7.75 (d, J=7.4 Hz, 4H), 7.80 (d, J=8.5 Hz, 4H), 7.85 (t, J=8.2 Hz, 1H), 8.16 (d, J=8.0 Hz 8H), 8.22 (d, J=2.0 Hz, 2H), 8.32 (d, J=2.0 Hz, 4H). Positive FAB-MS: m/z 1796 [M]$^+$. IR (KBr disk): 2148 cm$^{-1}$ ν(C≡C). Elemental analyses: Found (%): C, 78.11; H, 4.71; N, 6.29. Calcd for C$_{117}$H$_{83}$N$_8$Au: C, 78.15; H, 4.65; N, 6.23.

Compound 8: [Au($^t$BuC^N^C$^t$Bu-ligand L8)]. Yield: 30 mg, 22%. $^1$H NMR (500 MHz, CD$_2$Cl$_2$, 298 K, relative to Me$_4$Si): δ 1.26 (s, 18H), 7.24-7.28 (m, 16H), 7.34 (dd, J=8.0 and 2.0 Hz, 2H), 7.37-7.48 (m, 32H), 7.48 (dd, J=8.5 and 2.4 Hz, 4H), 7.58 (d, J=8.0 Hz, 2H), 7.62 (dd, J=8.5 and 2.0 Hz, 8H), 7.71-7.75 (m, 14H), 7.84 (d, J=8.5 Hz, 4H), 7.87 (t, J=8.4 Hz, 1H), 7.91 (dd, J=8.6 and 2.0 Hz, 4H), 7.96 (d, J=8.6 Hz, 4H), 8.16 (d, J=8.0 Hz, 16H), 8.23 (d, J=2.4 Hz, 2H), 8.34 (d, J=2.0 Hz, 8H), 8.60 (d, J=2.0 Hz, 4H). Positive FAB-MS: m/z 3119 [M]$^+$. IR (KBr disk): 2148 cm$^{-1}$ ν(C≡C). Elemental analyses: Found (%): C, 81.57; H, 4.77; N, 7.02. Calcd for C$_{213}$H$_{139}$N$_{16}$Au·½H$_2$O: C, 81.77; H, 4.51; N, 7.16.

Compound 9: [Au($^t$BuC^N^C$^t$Bu-ligand L4)]. Yield: 106 mg, 70%. $^1$H NMR (500 MHz, CD$_2$Cl$_2$, 298 K, relative to Me$_4$Si): δ 1.40 (s, 18H), 1.46 (s, 36H), 7.30 (d, J=8.6 Hz, 2H), 7.33 (dd, J=8.2 and 1.8 Hz, 2H), 7.43-7.48 (m, 10H), 7.50-7.54 (m, 8H), 7.58 (d, J=8.2 Hz, 2H), 7.62 (d, J=8.6 Hz, 2H), 7.87 (t, J=8.0 Hz, 1H), 8.16 (d, J=1.8 Hz, 4H), 8.21 (d, J=2.0 Hz, 2H). Positive FAB-MS: m/z 1360 [M]$^+$. IR (KBr disk): 2146 cm$^{-1}$ ν(C≡C). Elemental analyses: Found (%): C, 74.46; H, 6.69; N, 3.87. Calcd for C$_{85}$H$_{87}$N$_4$Au·½H$_2$O: C, 74.48; H, 6.47; N, 4.28.

Compound 10: [Au(C^N^C-ligand L4)]. Yield: 120 mg, 83%. $^1$H NMR (500 MHz, DMSO-d$_6$, 298 K, relative to Me$_4$Si): δ 1.47 (s, 36H), 7.28-7.32 (m, 4H), 7.41-7.45 m, 10H), 7.50-7.53 (m, 8H), 7.56 (d, J=8.0 Hz, 2H), 7.61 (d, J=8.4 Hz, 2H), 7.65 (dd, J=8.0 and 1.0 Hz, 2H), 7.93 (t, J=8.0 Hz, 1H), 8.08 (dd, J=7.2 and 1.0 Hz, 2H), 8.16 (d, J=1.6 Hz, 4H). Positive FAB-MS: m/z 1248 [M]$^+$. IR (KBr disk): 2148 cm$^{-1}$ ν(C≡C). Elemental analyses: Found (%): C, 73.48; H, 5.53; N, 4.43. Calcd for C$_{77}$H$_{71}$N$_4$Au·½H$_2$O: C, 73.49; H, 5.76; N, 4.45.

Compound 11: [Au(2,5-F$_2$—C$_6$H$_3$—C^N^C-ligand L9)]. Yield: 100 mg, 58%. $^1$H NMR (400 MHz, CDCl$_3$, 298 K, relative to Me$_4$Si): δ 1.46 (s, 144H), 7.23-7.36 (m, 21H), 7.45-7.47 (m, 20H), 7.61-7.70 (m, 24H), 7.77-7.80 (m, 6H,), 7.82-7.94 (m, 8H), 8.16-8.19 (m, 18H), 8.28 (d, J=1.4 Hz, 8H), 8.58 (s, 4H). Positive FAB-MS: m/z 4017 [M]$^+$. IR (KBr disk): 2146 cm$^{-1}$ ν(C≡C). Elemental analyses: Found (%): C, 80.26; H, 6.52; N, 5.37. Calcd for C$_{275}$H$_{253}$F$_2$N$_{16}$Au·1½CH$_2$Cl$_2$:C, 80.13; H, 6.23; N, 5.41.

Compound 12: [Au(C^N^C-ligand L10)]. Yield: 60 mg, 38%. $^1$H NMR (400 MHz, DMSO-d$_6$, 298 K, relative to Me$_4$Si): 6.96-7.08 (m, 18H), 7.14 (d, J=8.0 Hz, 4H), 7.26-

7.34 (m, 10H), 7.37 (t, J=8.0 Hz, 2H), 7.43 (d, J=8.0 Hz, 2H), 7.48-7.63 (m, 8H), 7.87-7.91 (m, 4H), 7.96 (d, J=8.0 Hz, 2H), 8.17 (t, J=8.0 Hz, 1H). Positive FAB-MS: m/z 1181 [M]$^+$.

Compound 13: [Au(dpiq-ligand L10)]. Yield: 30 mg, 45%. $^1$H NMR (500 MHz, DMSO-d$_6$, 298 K, relative to Me$_4$Si): 7.01-7.08 (m, 18H), 7.13 (d, J=8.0 Hz, 4H), 7.29-7.60 (m, 22H), 7.61 (t, J=5.0 Hz, 1H), 7.84-7.94 (m, 3H), 7.95 (d, J=5.0 Hz, 1H), 8.07 (d, J=5.0 Hz, 1H), 8.41 (d, J=10.0 Hz, 1H), 8.50 (s, 1H), 8.94 (d, J=10.0 Hz, 1H). Positive FAB-MS: m/z 1231 [M]$^+$.

Example 3

UV-Vis Absorption Properties

The UV-vis absorption spectra of compounds 1-13 in dichloromethane at 298 degrees K feature an intense absorption band at 240-375 nm and a moderately intense vibronic-structured absorption band at ca. 380-450 nm with extinction coefficients (ϵ) on the order of $10^4$ dm$^3$mol$^{-1}$ cm$^{-1}$. The UV-visible absorption data of compounds 1-13 in dichloromethane at 298 K have been summarized in Table 1.

Figure 3:
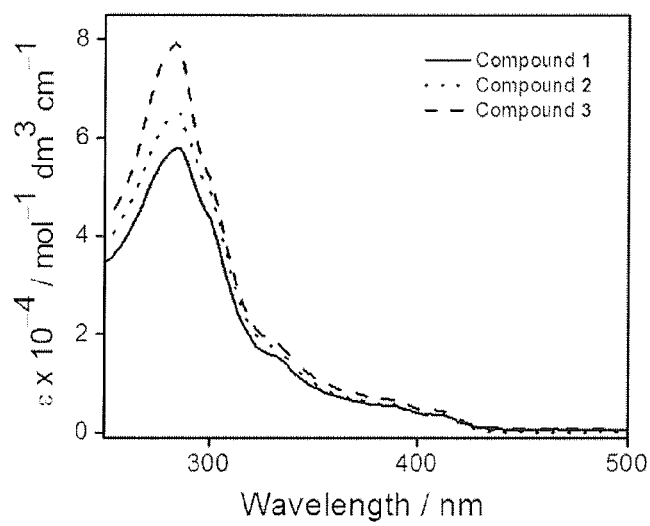
FIG. 3 shows the UV-Visible absorption spectra of compounds 1-3 in dichloromethane at 298 degrees K, in accordance with an embodiment of the present invention.

As shown in FIG. 3, compounds 1-3 show an intense absorption band at 250-290 nm and a moderately intense vibronic-structured band at ca. 370-410 nm in dichloromethane at 298 degrees K. The high energy band is assigned to the spin-allowed intraligand (IL) π→π* transition of the benzyloxy units. The molar extinction coefficients at approximately 285 nm increased from compound 1 to compound 3, which is ascribed to the increased number of benzyloxy units. For instance, the extinction coefficients (ϵ) at 285 nm for compounds 1, 2 and 3 are 5.77×10$^4$, 6.48×10$^4$ and 7.93×10$^4$ dm$^3$ mol$^{-1}$ cm$^{-1}$ respectively. The low-energy vibronic-structured band shows vibrational progressional spacings of ca. 1300 cm$^{-1}$, corresponding to the skeletal vibrational frequency of the 2,5-F$_2$—C$_6$H$_3$—C^N^C ligand. The low-energy absorptions are assigned as IL π→π* transition of the 2,5-F$_2$—C$_6$H$_3$—C^N^C ligand.

Figure 4:
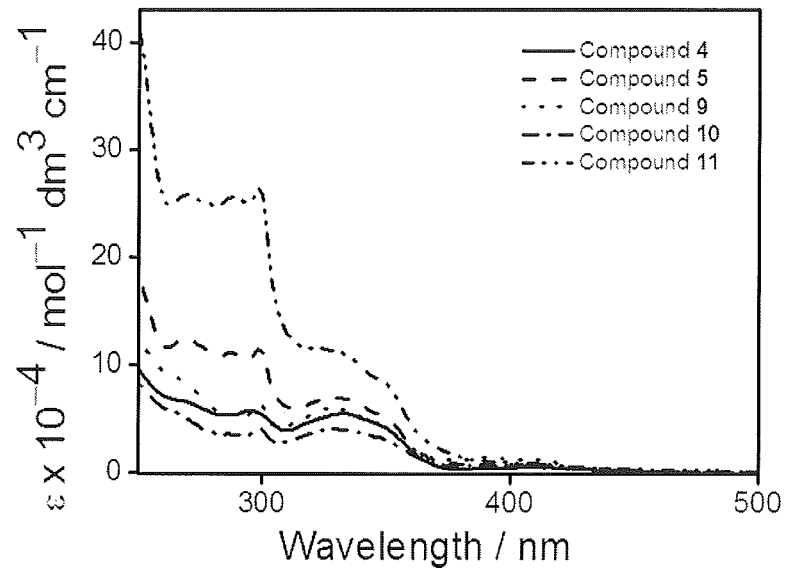
FIG. 4 shows the UV-Visible absorption spectra of compounds 4, 5, 9, 10 and 11 in dichloromethane at 298 degrees K, in accordance with an embodiment of the present invention.

FIG. 4 shows the electronic absorption spectra of compounds 4, 5, 9, 10, and 11. Compounds 4, 5, 9-11 exhibit intense absorptions at 230-375 nm and a moderately intense vibronic-structured band at ca. 380-420 nm; it is noted that an additional absorption tail at 430-500 nm is observed in FIG. 4. The absorption bands at 230-375 nm are mainly attributed to spin-allowed IL π→π* transition of the carbazole units. Similar to other gold (III) compounds, the weaker vibronic-structured absorption band was tentatively assigned to a metal-perturbed IL π→π* transition of the RC^N(R')^CR ligand with charge transfer character from the phenyl ring to the pyridyl unit. On the other hand, when 3,6-di-tert-butylcarbazole substituents are introduced at the 4,4' positions of the triphenylamine alkynyl moieties, electronic perturbation becomes so significant that ligand L4, L5 and L9 become more electron-rich, and the possibility of an admixture of IL πΘπ*[RC^N(R')^CR] and alkynyltriarylamine] or a ligand-to-ligand charge transfer (LLCT) π[alkynyltriarylamine]→π*[RC^N(R')^CR] transition is likely.

Figure 5:
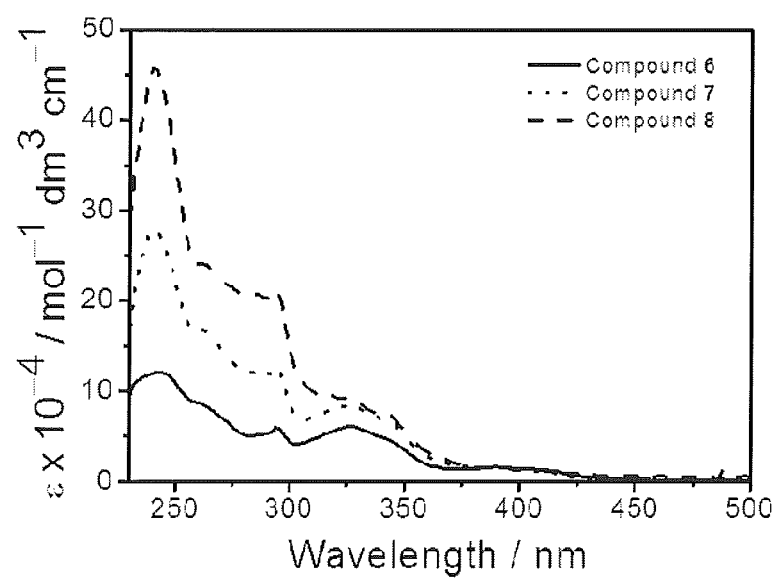
FIG. 5 shows the UV-Visible absorption spectra of compounds 6-8 in dichloromethane at 298 degrees K, in accordance with an embodiment of the present invention.
Figure 6:
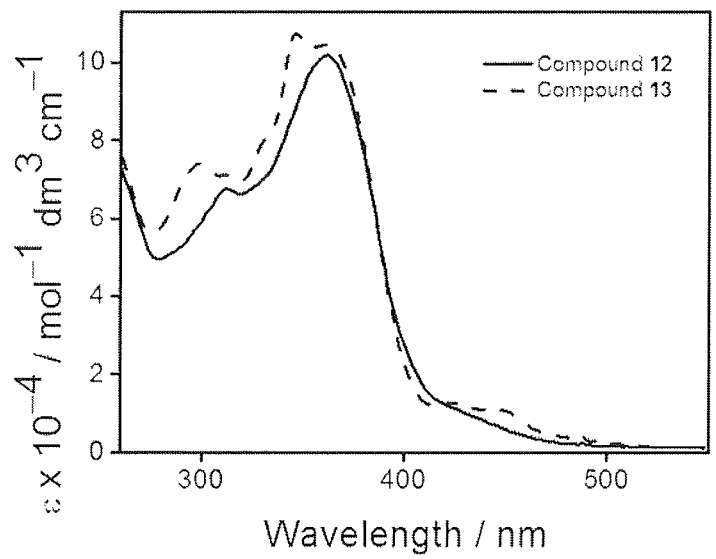
FIG. 6 shows the UV-Visible absorption spectra of compounds 12 and 13 in dichloromethane at 298 degrees K, in accordance with an embodiment of the present invention.

FIGS. 5 and 6 show the electronic absorption spectra of compounds 6-8, and the electronic absorption spectra of compounds 12-13, respectively. Compounds 6-8 show intense absorption bands at 300-350 nm and a moderately intense vibronic-structured shoulder at ca. 390-410 nm; while compounds 12-13 exhibit strong absorption bands at ca. 300-380 nm. Moreover, a lower energy band can be observed at ca. 430-450 nm in compound 13. The UV-vis absorption and emissive spectra of compounds 1-13 in Examples 3 and 4, respectively, gave the fundamental photophysical data, that provide useful guidelines for the design of the chemical structures to tune the emission color of the emitters in both solution and solid state.

Example 4

Photoluminescence Properties

Figure 7:
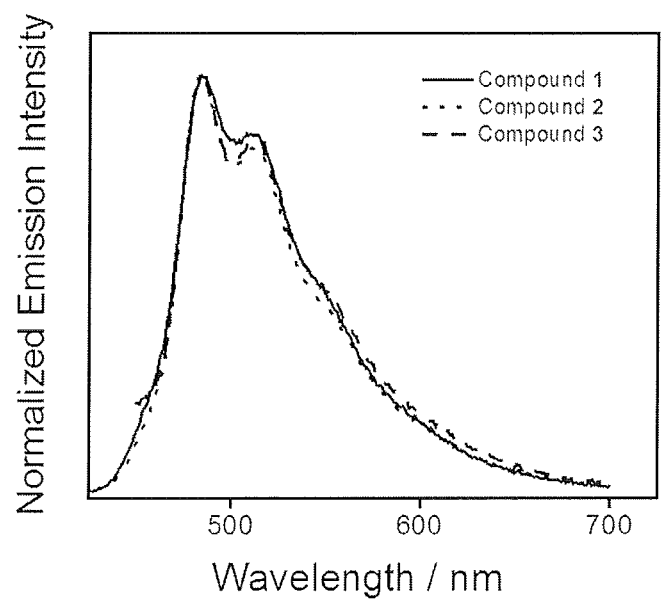
FIG. 7 shows the normalized photoluminescence spectra of compounds 1-3 in dichloromethane at 298 degrees K, in accordance with an embodiment of the present invention. No instrumental correction was applied for the emission wavelength.

Unlike most other Au(III) compounds which are non-emissive or only show luminescence at low temperatures, compounds 1-13 display intense luminescence at 482-695 nm in solution at room temperature (Table 1). FIG. 7 shows the normalized emission spectra of compounds 1-3. Upon excitation at λ=380 nm in dichloromethane solution at 298 degrees K, a vibronic-structured emission band with a band maximum at around 480 nm is observed for compounds 1-3. Interestingly, the introduction of an increasing content of polyarylether dendrons onto the alkynyl moiety results in a minor perturbation in the emission maxima. The progressional spacings of ca. 1300 cm$^{-1}$, that are characteristic of the C≡C and C=N stretching frequencies of the 2,5-F$_2$—C$_6$H$_3$—C^N^C tridentate ligand, indicate the involvement of the tridentate ligand in the excited state origin. According the published literature concerning the luminescence of related compounds, the luminescences of compounds 1-3 are assigned assuming that they originate from a metal-perturbed IL $^3$[π→π*] state of the 2,5-F$_2$—C$_6$H$_3$—C^N^C tridentate ligand, probably mixed with a charge transfer character from the phenyl ring to the pyridyl unit.

Figure 8:
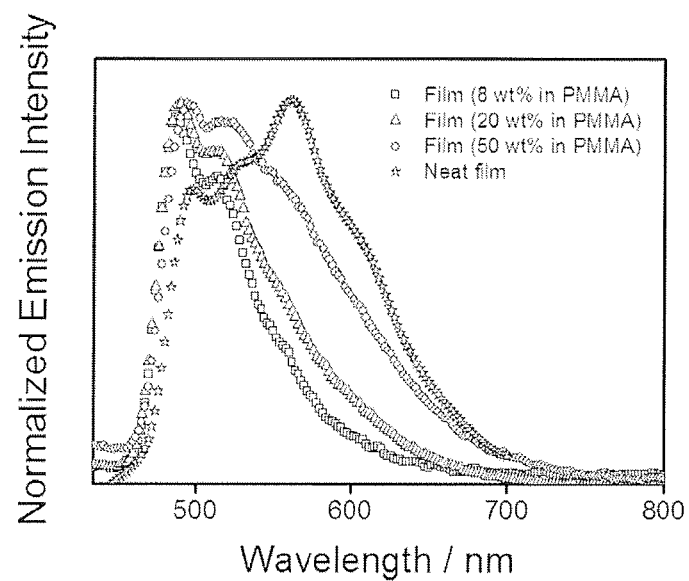
FIG. 8 shows the normalized photoluminescence spectra of thin films of compound 2 doped into PMMA at different concentrations (wt %) at 298 degrees K, in accordance with an embodiment of the present invention. No instrumental correction was applied for the emission wavelength.
Figure 9:
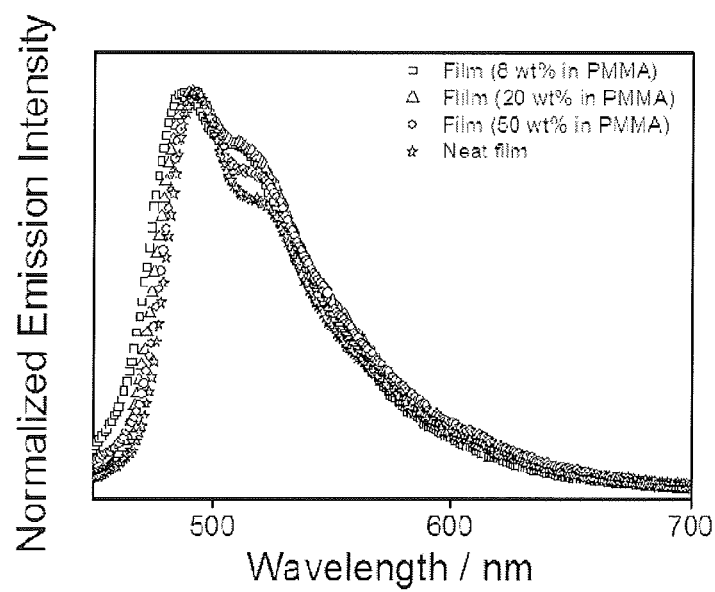
FIG. 9 shows the normalized photoluminescence spectra of thin films of compound 3 doped into PMMA at different concentrations (wt %) at 298 degrees K, in accordance with an embodiment of the present invention. No instrumental correction was applied for the emission wavelength.

FIGS. 8 and 9 display the normalized emission spectra of thin films of compounds 2 and 3 doped into a PMMA substrate at different concentrations. Both compounds show similar vibronic-structured emission bands with an emission energy similar to that observed for compound 2 in dichloromethane solution. The emissive origin is tentatively assigned assuming that it originates from a metal-perturbed IL $^3$[π→π*] state of the 2,5-F$_2$—C$_6$H$_3$—C^N^C ligand. In contrast to the insignificant change of emission properties in dichloromethane solution, the saturated polyarylether dendrons dramatically influence the solid-state emission of the dendritic Au(III) compounds. A red emission tail is observed for compound 2 with increasing dopant concentrations from 8 wt % to 50 wt %, and it is more pronounced in the neat film. This observation could be due to the excimeric emission resulting from the π-stacking of the 2,5-F$_2$—C$_6$H$_3$—C^N^C moieties with higher order and better packing of molecules at higher concentrations. The bathochromic problem is greatly alleviated by the introduction of the second generation of polyarylether dendrons onto the alkynyl moiety in compound 3. It can be seen in FIG. 9 that with increasing dopant concentrations of compound 3 from 8 wt % to 50 wt % and even up to 100 wt % (i.e. neat film), the red emission tail has disappeared. The emission band of compound 3 in the 50 wt % dopant concentration is almost the same as that in the solution, suggesting that the π-stacking of the 2,5-F$_2$C$_6$H$_3$—C^N^C moieties between the emissive cores has been reduced. The use of saturated polyarylether dendrons to prevent the π-stacking of the 2,5-F$_2$C$_6$H$_3$—C^N^C moieties and hence the formation of eximeric emission in order to maintain the colour purity and stability of the Au(III) chromophoric compounds is first demonstrated. In some embodiments of the present invention, π-stacking of the 2,5-F$_2$C$_6$H$_3$—C^N^C moieties is prevented by polyarylether dendrons, and effectively minimizes the intermolecular interactions between the molecules that lead to emission quenching or triplet-triplet annihilation. This emission quenching would otherwise inevitably degrade the performance of the OLED.

Figure 10:
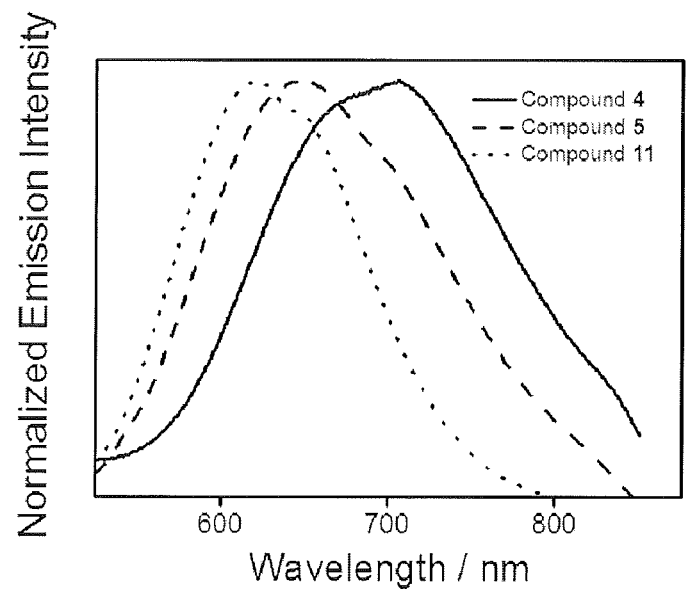
FIG. 10 shows the photoluminescence spectra of compounds 4, 5 and 11 in dichloromethane at 298 degrees K, in accordance with an embodiment of the present invention. No instrumental correction was applied for the emission wavelength.
Figure 11:
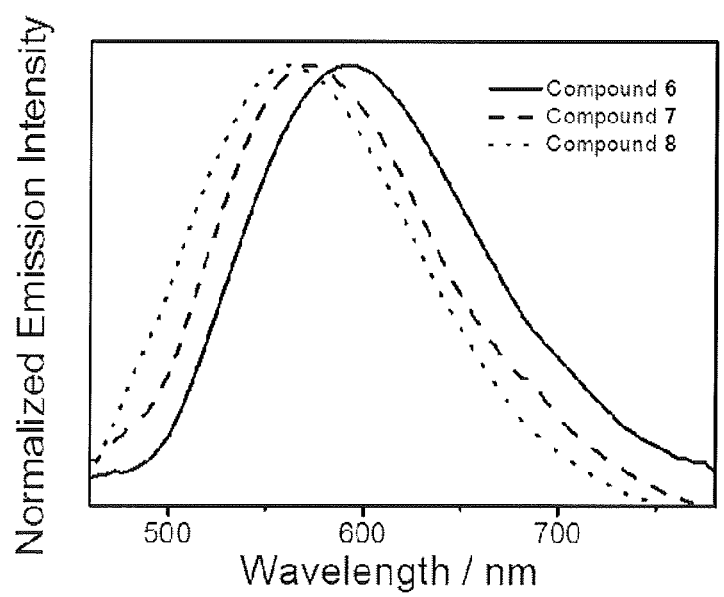
FIG. 11 shows the normalized photoluminescence spectra of compounds 6-8 in dichloromethane at 298 degrees K, in accordance with an embodiment of the present invention. No instrumental correction was applied for the emission wavelength.

FIGS. 10 and 11 show the normalized emission spectra of compounds 4, 5, 11 and normalized emission spectra of compounds 6-8 in dichloromethane at room temperature, respectively. Upon excitation at λ>380 nm, a broad structureless emission band is observed at ca. 560-695 nm. Due to the presence of the electron-donating triphenylamine substituent on the ligand L4-L9 moieties, the origin of the emission band in compounds 4-8 and 11 is tentatively assigned as derived from an excited state of $^3$LLCT π[alkynyltriarylamine→π* [RC^N(R')^CR] origin. Interestingly, incorporation of the triphenylamine moiety into the higher generation of dendrimers for compounds 6-8 has resulted in higher-energy emission bands [6 (591 nm)<7 (570 nm)<8 (560 nm)]. Similarly compounds 4, 5 and 11 exhibit progressively higher emission bands [4 (695 nm)<5 (646 nm)<11 (620 nm)].

Figure 12:
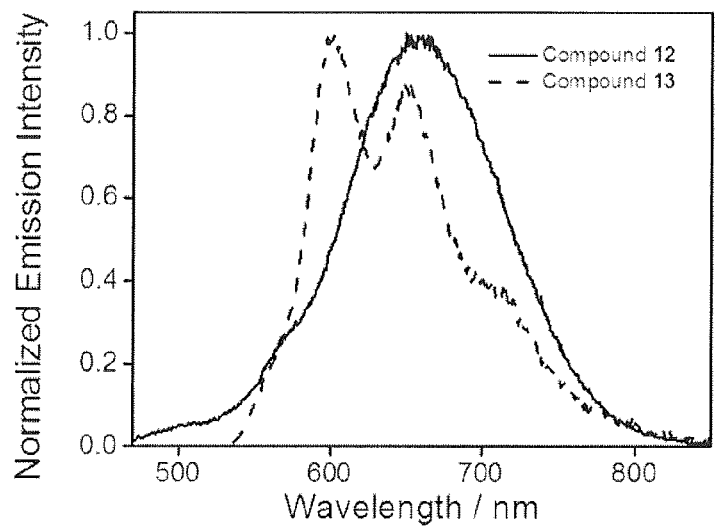
FIG. 12 shows the normalized photoluminescence spectra of compounds 12 and 13 in dichloromethane at 298 degrees K, in accordance with an embodiment of the present invention. No instrumental correction was applied for the emission wavelength.

FIG. 12 shows the normalized photoluminescence spectra of compounds 12 and 13 in dichloromethane at 298 degrees K. A vibronic-structured band with a band maximum at around 600 nm is observed for compound 12 and a broad lower energy structureless emission band centered at 660 nm is noted for compound 13.

Figure 13:
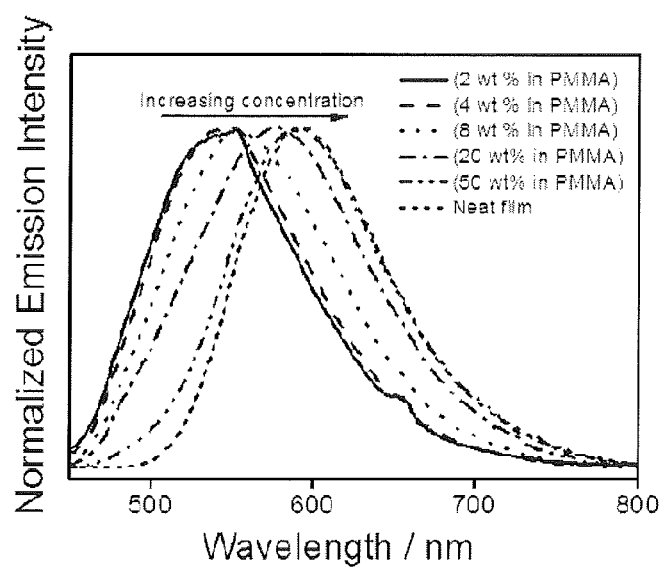
FIG. 13 shows the normalized photoluminescence spectra of thin films of compound 4 doped into PMMA at different concentrations (wt %) at 298 degrees K, in accordance with an embodiment of the present invention. No instrumental correction was applied for the emission wavelength.
Figure 14:
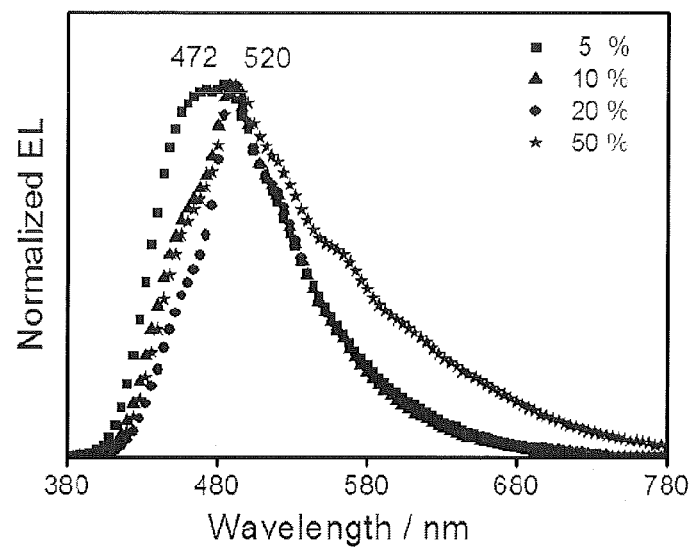
FIG. 14 shows the electroluminescence spectra of a device with compound 2 doped into MCP as the light-emitting layer, in accordance with an embodiment of the present invention.
Figure 15:
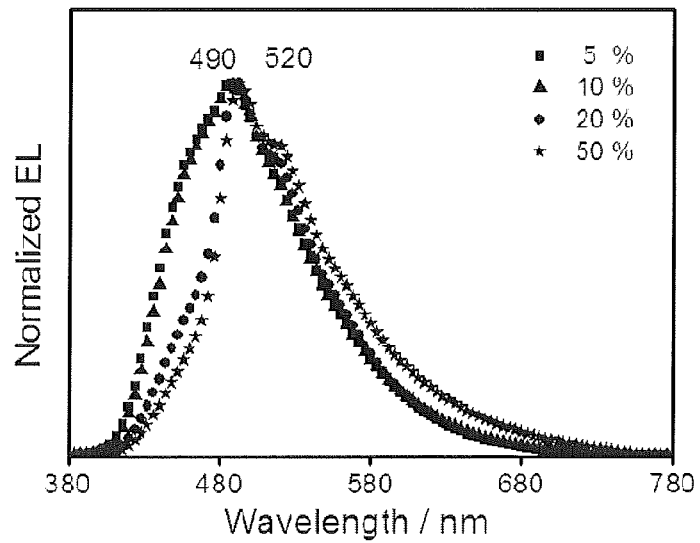
FIG. 15 shows the electroluminescence spectra of a device with compound 3 doped into MCP as the light-emitting layer, in accordance with an embodiment of the present invention.
Figure 16:
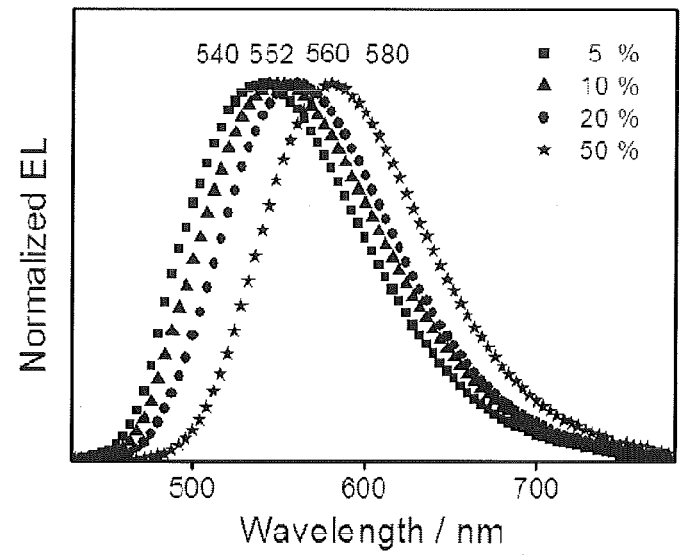
FIG. 16 shows the electroluminescence spectra of device with compound 4 doped into MCP as the light-emitting layer, in accordance with an embodiment of the present invention.
Figure 17:
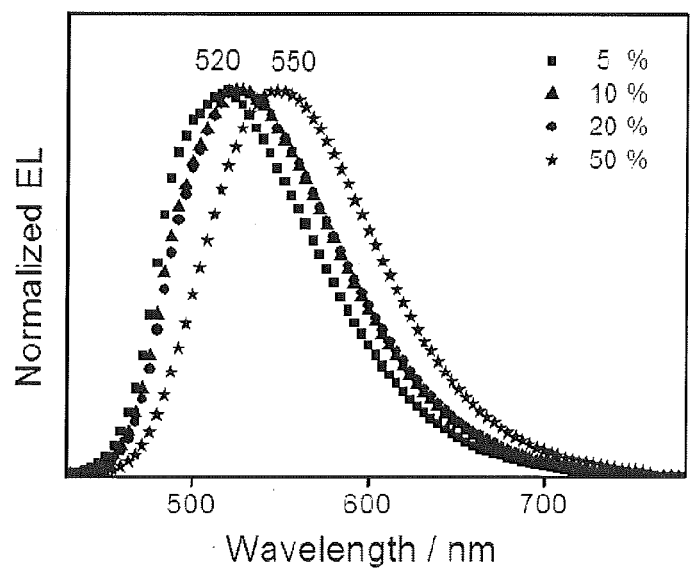
FIG. 17 shows the electroluminescence spectra of a device with compound 5 doped into MCP as the light-emitting layer, in accordance with an embodiment of the present invention.
Figure 18:
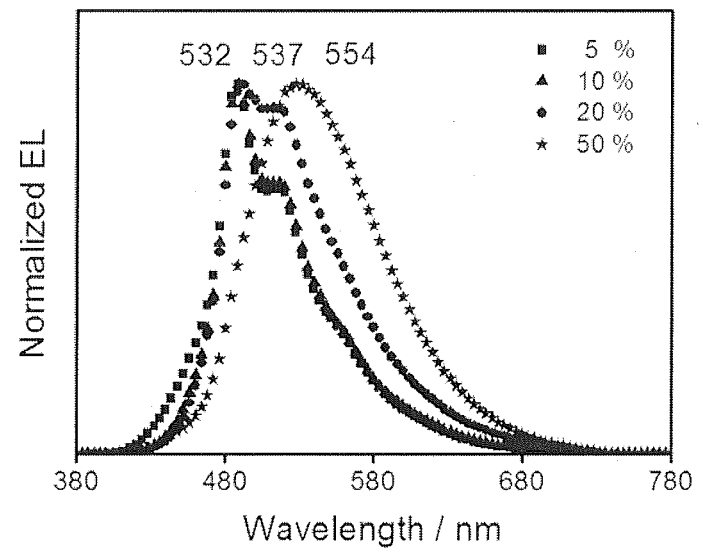
FIG. 18 shows the electroluminescence spectra of a device with compound 6 doped into MCP as the light-emitting layer, in accordance with an embodiment of the present invention.
Figure 19:
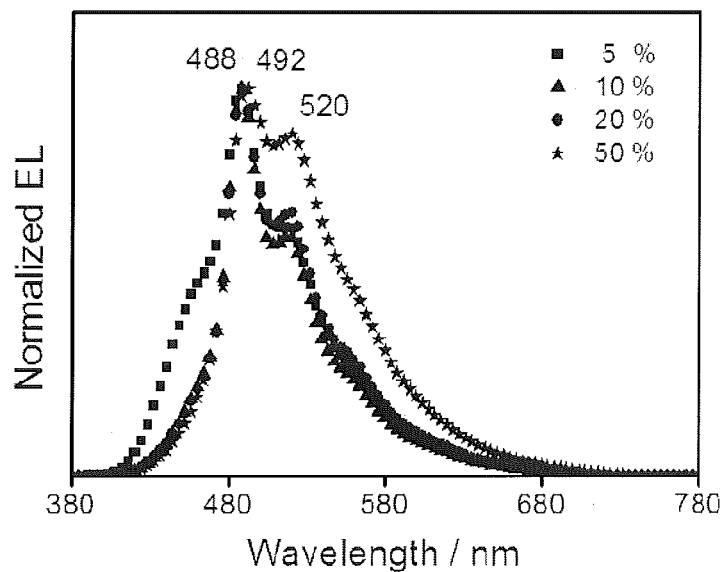
FIG. 19 shows the electroluminescence spectra of a device with compound 7 doped into MCP as the light-emitting layer, in accordance with an embodiment of the present invention.
Figure 20:
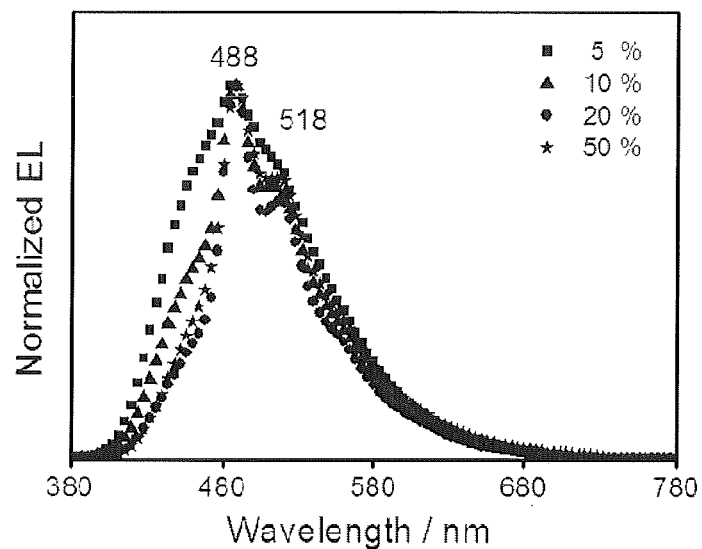
FIG. 20 shows the electroluminescence spectra of a device with compound 8 doped into MCP as the light-emitting layer, in accordance with an embodiment of the present invention.
Figure 21:
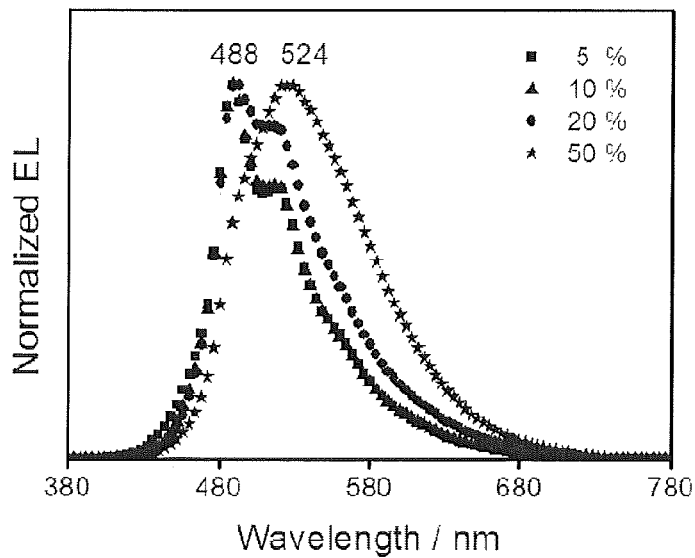
FIG. 21 shows the electroluminescence spectra of a device with compound 9 doped into MCP as the light-emitting layer, in accordance with an embodiment of the present invention.
Figure 22:
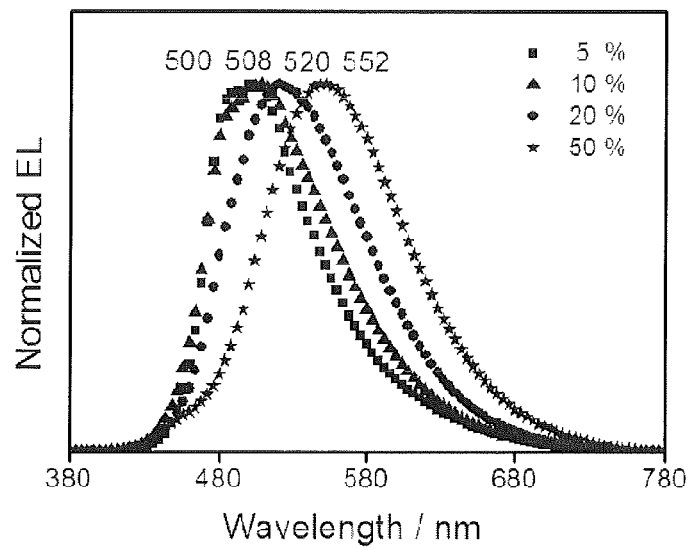
FIG. 22 shows the electroluminescence spectra of device with compound 10 doped into MCP as the light-emitting layer, in accordance with an embodiment of the present invention.
Figure 23:
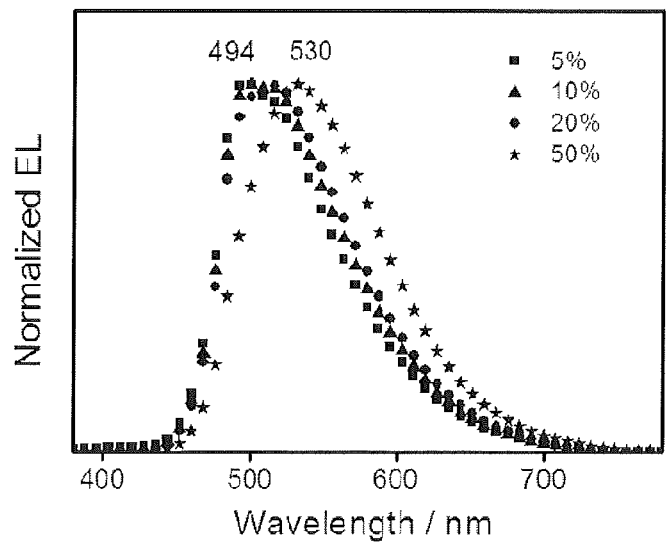
FIG. 23 shows the electroluminescence spectra of device with compound 11 doped into MCP as the light-emitting layer, in accordance with an embodiment of the present invention.
Figure 24:
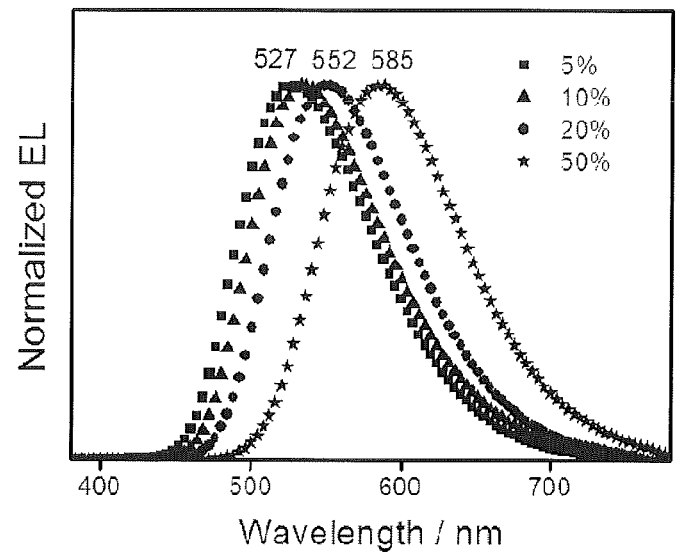
FIG. 24 shows the electroluminescence spectra of device with compound 12 doped into MCP as the light-emitting layer, in accordance with an embodiment of the present invention.
Figure 25:
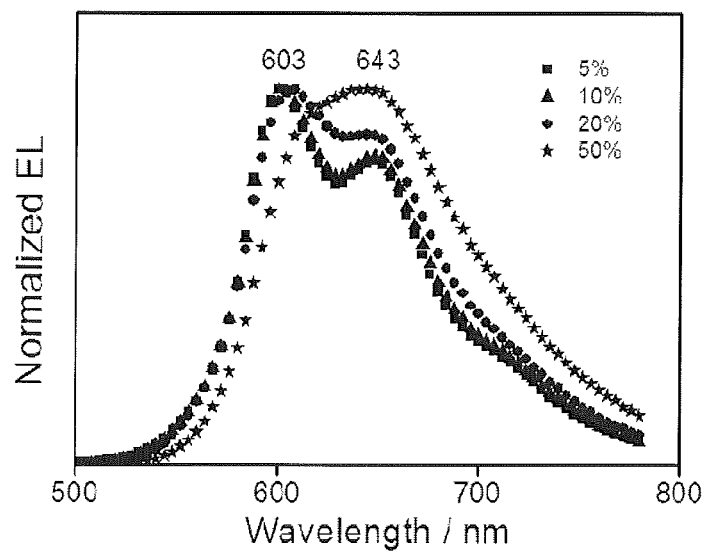
FIG. 25 shows the electroluminescence spectra of device with compound 13 doped into MCP as the light-emitting layer, in accordance with an embodiment of the present invention.

FIG. 13 depicts the emission spectra of thin films of compound 4 doped into PMMA at different concentrations. A red shift in the emission band between 540 and 590 nm is observed with increasing dopant concentrations from 2 wt % to 50 wt %. The emission maximum in the neat film is almost identical to that in the 50 wt % thin film at around 591 nm, suggesting that the extent of π-stacking of the 2,5-F$_2$—C$_6$H$_3$—C^N^C moieties of compound 4 with increasing dopant concentration from 50 wt % to 100% (i.e. neat film) is similar. Such concentration-dependent emission has also been observed for other structurally related Au(III) compounds, probably due to dimeric/oligomeric or excimeric emission in the thin film arising from the π-π stacking of the 2,5-F$_2$—C$_6$H$_3$—C^N^C ligand. This concentration-dependent colour tuning can be accomplished by making use of the relationship between the emission colour of the OLED and the dopant concentration, and thus providing an optimal emission colour spectrum for an application for which the OLED will be used.

TABLE 1

Photophysical data for compounds 1-13

| Compound | Medium (T/K) | Absorption λ$_{max}$/nm (λ$_{max}$/dm$^3$mol$^{-1}$cm$^{-1}$) | Emission λ$_{max}$/ nm(τ$_o$/μs) | Φ$_{sol}$[a] | Φ$_{film}$(%)[b] |
|---|---|---|---|---|---|
| 1 | CH$_2$Cl$_2$ (298) | 285 (56850), 330 (15820), 365 (6825), 390 (5340), 410 (3660) | 482, 512 (<0.1) | 4 × 10$^{-3}$ | [c] |
| 2 | CH$_2$Cl$_2$ (298) | 285 (64800), 330 (17570), 365 (7170), 390 (5705), 410 (3706) | 482, 512 (<0.1) | 7 × 10$^{-3}$ | 0.16 |
| 3 | CH$_2$Cl$_2$ (298) | 285 (79250), 330 (18870), 365 (8490), 390 (6515), 410 (4465) | 482, 512 (<0.1) | 9 × 10$^{-3}$ | 0.20 |
| 4 | CH$_2$Cl$_2$ (298) | 242 (114410), 300 (54050), 330 (64500), 350 (41940), 390 (4740), 410 (5850) | 695 (<0.1) | 3 × 10$^{-3}$ | 0.57 |
| 5 | CH$_2$Cl$_2$ (298) | 244 (233310), 290 (108980), 302 (95340), 330 (69580), 350 (51510), 386 (7830), 408 (7585) | 646 (<0.1) | 0.10 | 0.39 |
| 6 | CH$_2$Cl$_2$ (298) | 243 (121150), 262 (85205), 295 (58750), 327 (60250), 344 (45430), 391 (15830), 411 (12320) | 591 (0.13) | 0.13 | 0.17 |
| 7 | CH$_2$Cl$_2$ (298) | 243 (267750), 262 (168070), 295 (122600), 327 (83120), 344 (67300), 391 (15490), 411 (10355) | 570 (0.14) | 9 × 10$^{-2}$ | 0.15 |
| 8 | CH$_2$Cl$_2$ (298) | 243 (435480), 262 (240790), 295 (203110), 327 (89210), 344 (73810), 391 (15290), 411 (11360) | 560 (0.13) | 3 × 10$^{-2}$ | 0.13 |
| 9 | CH$_2$Cl$_2$ (298) | 240 (142790), 267 (82950), 299 (65346), 328 (60178), 394 (14570), 414 (11860) | 610 (0.2) | 6 × 10$^{-2}$ | 0.20 |
| 10 | CH$_2$Cl$_2$ (298) | 250 (83740), 267 (53065), 299 (41255), 328 (40790), 383 (7210), 402 (7380) | 632 (<0.1) | 2 × 10$^{-2}$ | [c] |
| 11 | CH$_2$Cl$_2$ (298) | 244 (523880), 300 (257760), 330 (112970), 350 (71705), 386 (12210), 408 (9510) | 620 (<0.1) | 1 × 10$^{-2}$ | 0.28 |
| 12 | CH$_2$Cl$_2$ (298) | 312 (67670), 328 (68820), 362 (102045), 428 (10580) | 660 (<0.1) | 2 × 10$^{-3}$ | 0.20 |
| 13 | CH$_2$Cl$_2$ (298) | 300 (74215), 328 (77945), 346 (107635), 362 (104550), 430 (11890), 450 (10620) | 600, 650 (<0.1) | 2 × 10$^{-3}$ | 0.05 |

[a]The luminescence quantum yield, measured at room temperature using [Ru(bpy)$_3$]Cl$_2$ in aqueous state as the reference (excitation wavelength = 436 nm, Φ$_{lum}$ = 0.042)
[b]Φ$_{film}$ of Au(III) compounds doped into MCP excited at wavelength of 320 nm
[c]Not determined Example 5

An organic EL device according to an embodiment of the invention was constructed in the following manner:

a) A transparent anode ITO-coated borosilicate glass substrate (38 mm×38 mm) with sheet resistance of 30 Ω/square was ultrasonicated in the commercial detergent Decon 90, rinsed in deionized water having a resistivity of 18.2 mega-ohm for 15 minutes, and then dried in an oven at 120 degree C. for an hour. The substrate was next subjected to an UV-ozone treatment in a Jelight 42-220 UVO-Cleaner equipped with a mercury grid lamp for 15 minutes in order to increase the work function of the ITO-coated glass substrate for better hole injection into the organic layer.

b) A 40-nm thick PEDOT:PSS hole-transporting layer was spin-coated by using a Laurell WS-400Ez-6NPP-Lit2 single wafer spin processor at 7000 rpm for 30 seconds onto the ITO-coated glass substrate of step a and baked at 110 degree C. for 10 minutes in air.

c) A 30-nm thick light-emitting layer was spin-coated by using a Laurell WS-400Ez-6NPP-Lit2 single wafer spin processor at 6000 rpm for 25 seconds onto PEDOT:PSS layer of step b, and baked at 80 degree C. for 10 minutes in air, in which compound 2 was doped into light-emitting MCP layer at different concentrations in the range from 5 to 50%;

d) The substrate was put into a vacuum chamber, and the chamber was pumped down from 1 bar to $5\times10^{-6}$ mbar;

e) A 30-nm thick BAlq electron-transporting layer was deposited by thermal evaporation on doped CBP light-emitting layer.

f) A 0.8-nm thick LiF layer and a 80 nm thick Al layer were deposited by thermal evaporation on the BAlq layer to form an electron-injecting cathode.

BAlq, LiF and Al were prepared by thermal evaporation from tantalum boats by applying current through the tantalum boats. Deposition rates were monitored with a quartz oscillation crystal and a Sigma SQM-242 quartz crystal card and controlled at 0.1-0.2 nm s$^{-1}$ for both organic and metal layers. Current density-voltage-luminance characteristics of organic EL devices were measured with a programmable Keithley model 2420 power source and a Spectrascan PR 655 colorimeter under ambient air conditions. The devices exhibit vibronic-structured blue emission with a peak maximum at 472 nm and a maximum luminance of 670 cd m$^{-2}$.

Example 6

The same materials and processing procedures were employed as described in Example 5, except that compounds 3, 6-10 were doped into MCP as the light-emitting layer.

Example 7

The same materials and processing procedures were employed as described in Example 5, except compounds 4, 5, 11-13 were doped into MCP as the light-emitting layer. For compounds 4, 5 and 11, a 5 nm thick TmPyPB and a 30 nm thick 3TPYMB were used as the electron-transporting layers; while for compounds 12 and 13, a 30 nm thick BmPyPhB was used as the electron-transporting layer. FIGS. 14-25 depict the electroluminescence spectra of the resulting OLEDs with compounds 2-13 doped into MCP as light-emitting layer.

Figure 26:
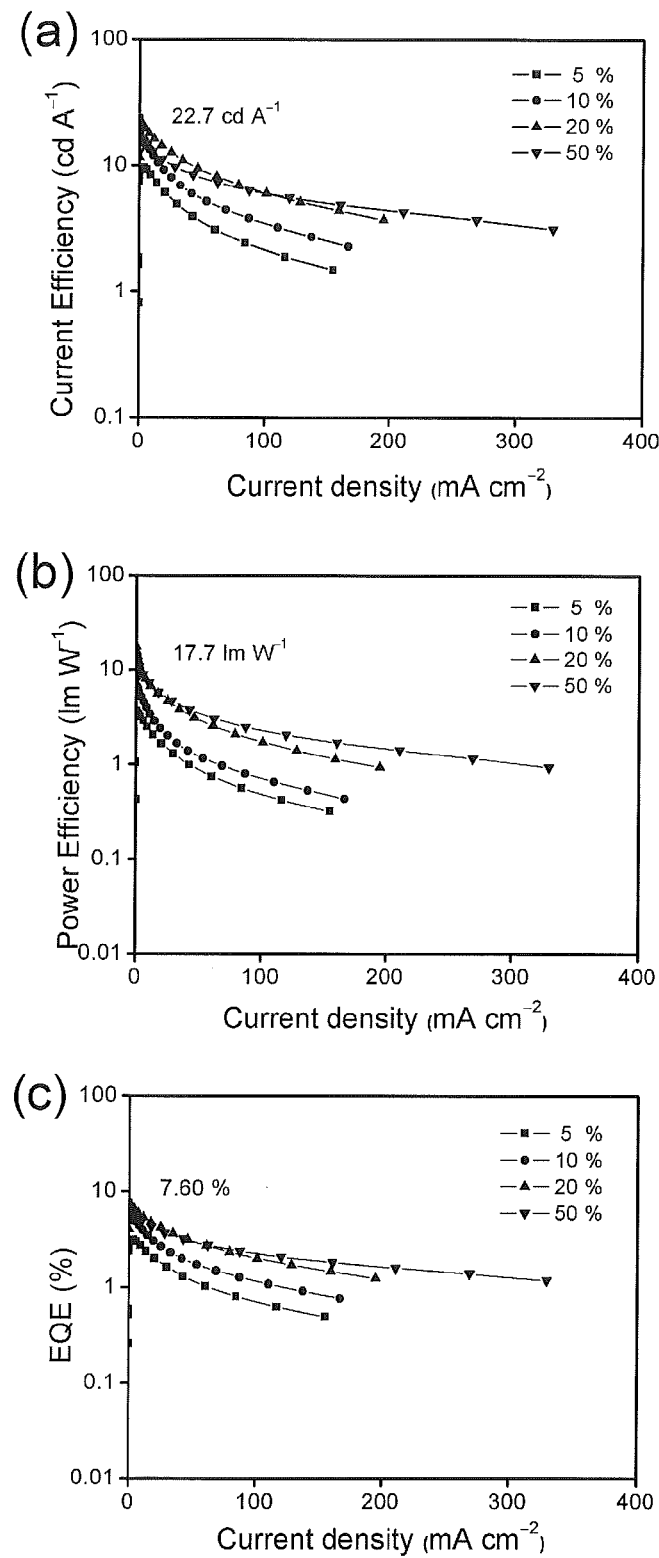
FIG. 26 shows a) current efficiency, b) power efficiency and c) external quantum efficiency of the device with compound 4 doped into MCP as the light-emitting layer, in accordance with an embodiment of the present invention.

Table 2 summarizes the performance of OLEDs with selected Au(III) compounds doped into MCP as the light-emitting layer. FIG. 26 shows a) current efficiency, b) power efficiency and c) external quantum efficiency of the device with compound 4 doped into MCP as the light-emitting layer. For an optimized device with 20% compound 4 doped into the MCP layer, high current, power, and external quantum efficiencies of 22.7 cd A$^{-1}$, 17.7 lm W$^{-1}$, and 7.60%, respectively, were obtained. These high device efficiencies are comparable to those of solution-processable OLEDs based on an iridium(III) system and are much higher than those of solution-processable OLEDs based on other transition metal centres, such as platinum(II), ruthenium(II) and rhenium(II) systems. In addition, such devices exhibit a broad and structureless yellow emission spectrum with excellent CIE coordinates of (0.49, 0.49). In some embodiments of the invention, these Au(III) dendrimers possess desirable electrophosphorescent properties, and are candidates as electrophosphorescent dopants for OLEDs.

TABLE 2

Characteristics of OLEDs using Au(III) compounds as phosphorescent dopants

| Compound | Max. Luminance (cd/m$^{-2}$) | Current Efficiency (cd/A$^{-1}$) | Power Efficiency (lm/W$^{-1}$) | EQE (%) |
|---|---|---|---|---|
| 2 | 670 | 3.3 | 1.3 | 1.2 |
| 3 | 800 | 6.7 | 3.5 | 2.5 |
| 4 | 10,300 | 22.7 | 17.7 | 7.6 |
| 5 | 2,200 | 21.9 | 16.4 | 7.0 |
| 6 | 2,800 | 10.6 | 6.1 | 3.7 |
| 7 | 1,700 | 4.7 | 3.3 | 1.6 |
| 8 | 1,100 | 1.0 | 0.6 | 0.4 |
| 9 | 4,300 | 13.7 | 10.8 | 4.3 |
| 10 | 3,100 | 16.1 | 12.6 | 5.1 |
| 11 | 900 | 11.4 | 9.6 | 3.8 |
| 12 | 3,800 | 20.0 | 16.4 | 6.3 |
| 13 | 650 | 1.2 | 0.8 | 0.9 |

These examples should not be construed as limiting the scope of the invention, but as providing illustrations of some of the embodiments of the invention.

What is claimed:

1. A luminescent gold(III) compound comprising the chemical structure represented by the following general formula,

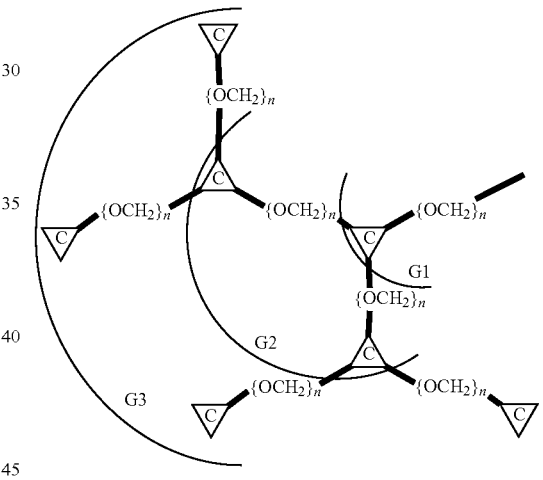

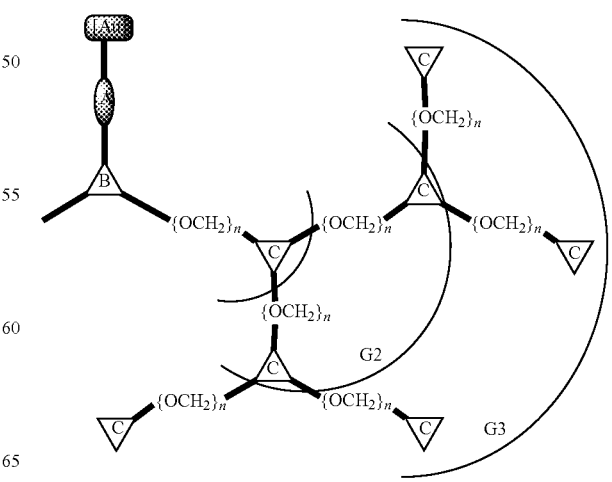

wherein:

(a) [Au] is a cyclometalated tridentate gold(III) group;
(b) Unit A is a σ-donating chemical group;
(c) Unit B is a central part of the dendrons comprising a branch point of component dendrimers;
(d) Unit C is optional surface groups or dendrons of the dendrimers;
(e) n=0 or 1.

2. The gold(III) compound according to claim 1, wherein unit A comprises at least one of alkylalkynyl, substituted alkylalkynyl, arylalkynyl, substituted arylalkynyl, heteroarylalkynyl and substituted heteroarylalkynyl.

3. The gold(III) compound according to claim 1, wherein unit B and C comprise benzene, phenyl derivatives, pyridine or pyridyl derivatives, with one or more alkyl, alkenyl, alkynyl, alkylaryl, cycloalkyl, OR, $NR_2$, SR, C(O)R, C(O)OR, $C(O)NR_2$, CN, $CF_3$, $NO_2$, $SO_2$, SOR, $SO_3R$, halo, aryl, substituted aryl, heteroaryl, substituted heteroaryl, heterocyclic group, wherein R is independently alkyl, alkenyl, alkynyl, alkyaryl, aryl, or cycloalkyl.

4. The gold(III) compound according to claim 1 wherein the compound is deposited as a thin layer on a substrate layer.

5. The gold(III) compound according to claim 4 wherein the thin layer including the compound is deposited by spin-coating, or inkjet printing.

6. The gold(III) compound according to claim 1, wherein the compound has photoluminescence properties within a range of about 380 to 1050 nm.

7. The gold(III) compound according to claim 1, wherein the compound emits light in response to the passage of an electric current or to a strong electric field.

8. A light-emitting device with an ordered structure comprising an anode, a hole-transporting layer, a light-emitting layer, an electron-transporting layer and a cathode wherein the light-emitting layer comprises a gold(III) compound having a chemical structure represented by the following general formula,

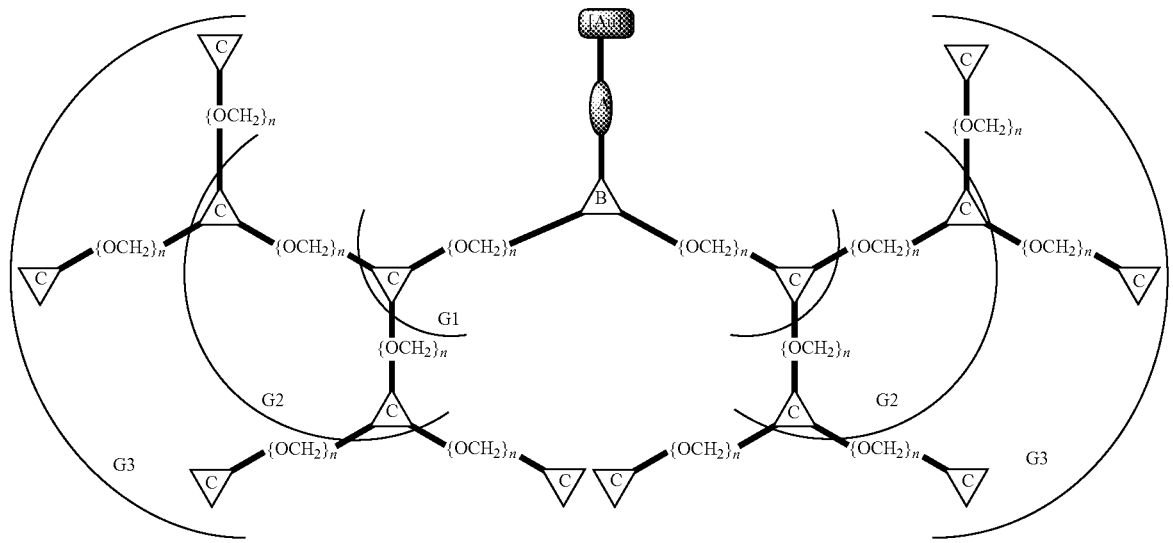

wherein:
(a) Unit A comprises at least one of alkylalkynyl, substituted alkylalkynyl, arylalkynyl, substituted arylalkynyl, heteroarylalkynyl, and substituted heteroarylalkynyl;
(b) Units B and optionally C comprise benzene, phenyl derivatives, pyridine or pyridyl derivatives, with one or more alkyl, alkenyl, alkynyl, alkylaryl, cycloalkyl, OR, $NR_2$, SR, C(O)R, C(O)OR, C(O)$NR_2$, CN, $CF_3$, $NO_2$, $SO_2$, SOR, $SO_3R$, halo, aryl, substituted aryl, heteroaryl, substituted heteroaryl, heterocyclic group, wherein R is independently alkyl, alkenyl, alkynyl, alkylaryl, aryl or cycloalkyl.

9. The light-emitting device according to claim 8, wherein the gold(III) compound therein serves as the light-emitting layer of the OLED.

10. The light-emitting device according to claim 8, wherein the gold(III) compound therein serves as a dopant in the light-emitting layer of the OLED.

11. The light-emitting device according to claim 8 wherein the emission energy of the light-emitting layer varies with the concentration of the gold(III) compound dopant.

12. A method for preparing a luminescent compound with a cyclometalated tridentate ligand and at least one strong σ-donating group coordinated to a gold(III) metal group, comprising the following reaction:

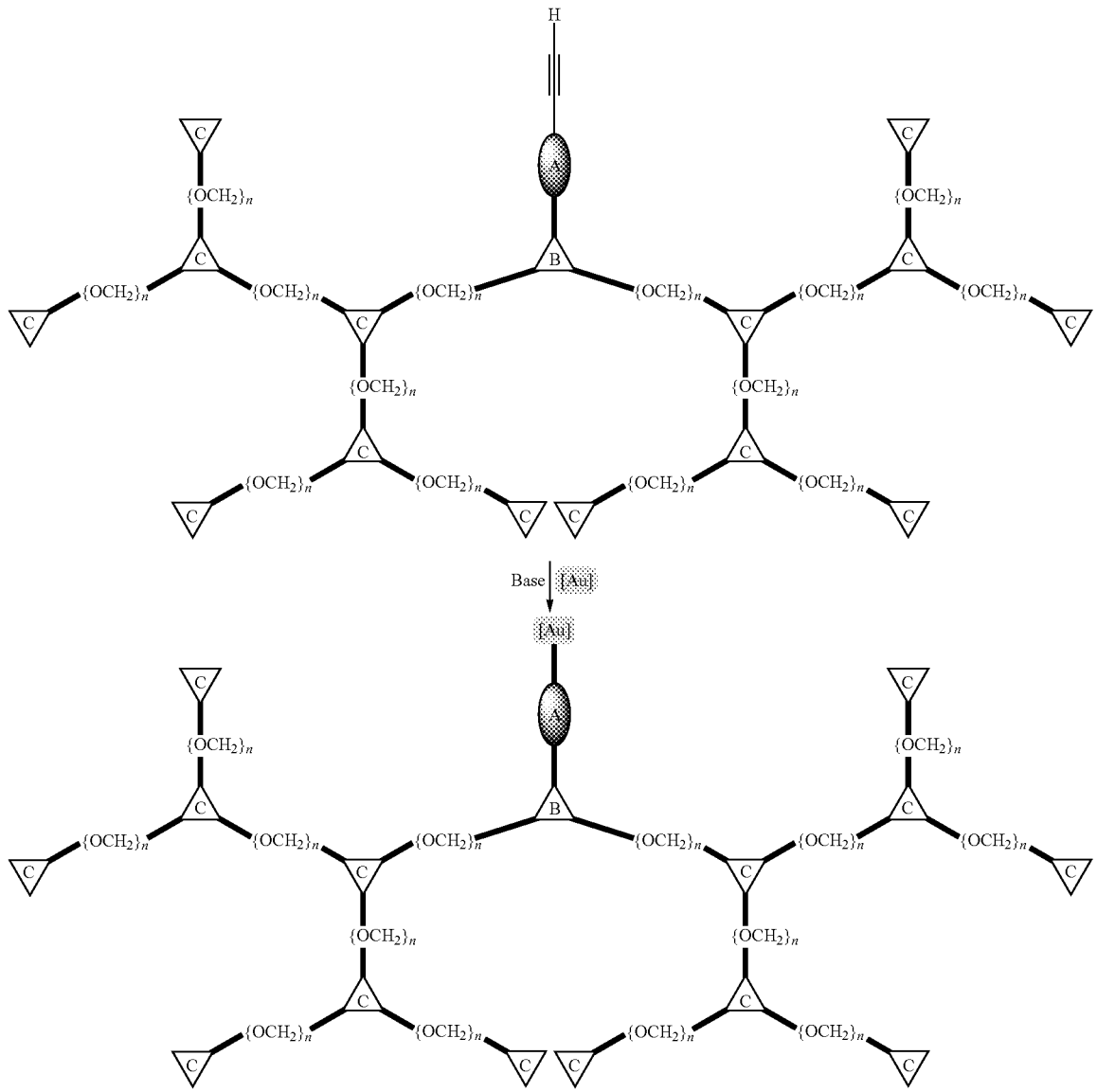

wherein:
(a) Unit A comprises at least one of alkylalkynyl, substituted alkylalkynyl, arylalkynyl, substituted arylalkynyl, heteroarylalkynyl, and substituted heteroarylalkynyl;
(b) Units B and optionally C comprise benzene, phenyl derivatives, pyridine or pyridyl derivatives, with one or more alkyl, alkenyl, alkynyl, alkylaryl, cycloalkyl, OR, $NR_2$, SR, C(O)R, C(O)OR, C(O)$NR_2$, CN, $CF_3$, $NO_2$, $SO_2$, SOR, $SO_3R$, halo, aryl, substituted aryl, heteroaryl, substituted heteroaryl, heterocyclic group, wherein R is independently alkyl, alkenyl, alkynyl, alkylaryl, aryl or cycloalkyl.

13. The method according to claim 12 wherein a luminescent compound is prepared.

14. The luminescent compound prepared according to the method of claim 12 wherein the compound includes a gold (III) metal group with a strong σ-donating group, said compound comprises a light-emitting layer that can be used with a light-emitting device.

15. The light-emitting device of according to claim 8 wherein the luminescent gold(III) metal compound is a dopant included in the light emitting layer of the light-emitting device.

16. The luminescent compound prepared according to the method of claim 12 wherein the gold(III) metal compound is a dopant that is used in a light emitting device.

17. The light-emitting device according to claim 8, wherein the gold(III) compound therein is used to fabricate an OLED.

18. The light-emitting device of claim 8 wherein the light-emitting layer is prepared using at least one solution processing technique.

19. A light-emitting device having an ordered structure comprising an anode, a hole-transporting layer, a light-emitting layer, an electron-transporting layer and a cathode wherein the light-emitting layer comprises a gold(III) compound prepared according to the method of claim 12.

20. The light-emitting device of claim 19 wherein the light-emitting layer is prepared using at least one solution processing technique.

* * * * *